(12) United States Patent
Niimi et al.

(10) Patent No.: US 12,312,643 B2
(45) Date of Patent: May 27, 2025

(54) METHOD FOR DETERMINING BACTERIAL NUMBER IN SPECIMEN

(71) Applicants: MITSUI CHEMICALS, INC., Tokyo (JP); NATIONAL UNIVERSITY CORPORATION UNIVERSITY OF TOYAMA, Toyama (JP)

(72) Inventors: Hideki Niimi, Toyama (JP); Isao Kitajima, Toyama (JP); Akio Miyakoshi, Toyama (JP); Yoshitsugu Higashi, Toyama (JP)

(73) Assignees: MITSUI CHEMICALS, INC., Tokyo (JP); NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 934 days.

(21) Appl. No.: 15/733,166

(22) PCT Filed: Jun. 21, 2018

(86) PCT No.: PCT/JP2018/023597
§ 371 (c)(1),
(2) Date: Jun. 3, 2020

(87) PCT Pub. No.: WO2019/123692
PCT Pub. Date: Jun. 27, 2019

(65) Prior Publication Data
US 2021/0102239 A1    Apr. 8, 2021

(30) Foreign Application Priority Data

Dec. 22, 2017  (JP) ................................ 2017-246333
Dec. 22, 2017  (JP) ................................ 2017-246724

(51) Int. Cl.
C12Q 1/68      (2018.01)
C12Q 1/686     (2018.01)
C12Q 1/689     (2018.01)

(52) U.S. Cl.
CPC ............. C12Q 1/689 (2013.01); C12Q 1/686 (2013.01)

(58) Field of Classification Search
CPC .................................. C12Q 1/686; C12Q 1/689
See application file for complete search history.

(56) References Cited

U.S. PATENT DOCUMENTS

2021/0032686 A1* 2/2021 Niimi ...................... C12Q 1/689
2021/0102239 A1* 4/2021 Niimi ...................... C12Q 1/686

FOREIGN PATENT DOCUMENTS

| CA | 2749693 A1 * | 7/2010 | ............. C12N 15/11 |
|----|--------------|--------|------|
| JP | 2009-268413 A | 11/2009 | |
| JP | 2016-192950 A | 11/2016 | |
| WO | 2007/097323 A1 | 8/2007 | |
| WO | 2010/007605 A1 | 1/2010 | |
| WO | 2010/082640 A1 | 7/2010 | |
| WO | 2015/053293 A1 | 4/2015 | |
| WO | WO-2018175399 A1 * | 9/2018 | ........... C12Q 1/6806 |

OTHER PUBLICATIONS

Frank et al., 2008. Critical evaluation of two primers commonly used for amplification of bacterial 16S rRNA genes. Applied and environmental microbiology, 74(8), pp. 2461-2470. (Year: 2008).*
Niimi et al., 2015. Melting temperature mapping method: A novel method for rapid identification of unknown pathogenic microorganisms within three hours of sample collection. Scientific reports, 5(1), pp. 1-13. (Year: 2015).*
Ott et al., 2004. Quantification of intestinal bacterial populations by real-time PCR with a universal primer set and minor groove binder probes: a global approach to the enteric flora. Journal of clinical microbiology, 42(6), pp. 2566-2572. (Year: 2004).*
Ueno et al., 2015. Eukaryote-made thermostable DNA polymerase enables rapid PCR-based detection of mycoplasma, ureaplasma and other bacteria in the amniotic fluid of preterm labor cases. PloS one, 10(6), e0129032, pp. 1-17. (Year: 2015).*
Barghouthi, S.A., 2011. A universal method for the identification of bacteria based on general PCR primers. Indian journal of microbiology, 51(4), pp. 430-444. (Year: 2011).*
Niimi et al., "Melting Temperature Mapping Method: A Novel Method for Rapid Identification of Unknown Pathogenic Microorganisms within Three Hours of Sample Collection," Scientific Reports, 2015, No. 5, No. 12543. (13 pages).
Higashi et al., "Spondylodiscitis due to Parvimonas micra diagnosed by the melting temperature mapping method: a case report," BMC Infectious Diseases, 2017, vol. 17, No. 584. (5 pages) (Cited on Extended European Search Report issued on Sep. 10, 2021, in corresponding European Patent Application No. 18890111.0).
Niimi, "Quick identification system for sepsis-inducing pathogenic bacteria", Clinical Microbiology, Sep. 2017, vol. 44, No. 5, pp. 63-71.
International Search Report (with an English translation) and Written Opinion issued on Sep. 18, 2018, in corresponding International Patent Application No. PCT/JP2018/0203597. (13 pages).

(Continued)

*Primary Examiner* — Gary Benzion
*Assistant Examiner* — Olayinka A Oyeyemi
(74) *Attorney, Agent, or Firm* — BUCHANAN INGERSOLL & IROONEY PC

(57) ABSTRACT

A method for enabling rapid and accurate determination of the number of bacterial cells in a specimen using a PCR method includes the following steps: (1) a first PCR step of carrying out a PCR method using a nucleic acid derived from a specimen as a template and a universal primer pair for amplifying a bacterial 16S rRNA gene to obtain a first amplification product; (2) a second PCR step of carrying out a nested PCR method using a primer pair(s) for amplifying an internal sequence(s) of the sequence of the first amplification product obtained by the first PCR step to obtain a second amplification product; and (3) a bacterial number determination step of obtaining the number of bacterial cells in the specimen based on the amount of the second amplification product obtained in the second PCR step and using calibration data.

23 Claims, 9 Drawing Sheets

Specification includes a Sequence Listing.

(56) References Cited

OTHER PUBLICATIONS

Michelow et al., "Diagnosis of *Streptococcus pneumoniae* Lower Respiratory Infection in Hospitalized Children by Culture, Polymerase Chain Reaction, Serological Testing, and Urinary Antigen Detection", Clinical Infectious Diseases, Jan. 1, 2022, vol. 34, No. 1, pp. e1-e11.

Niimi, "S1-1 Development of Quick Genetic Inspection System with Bacterial Count as a Novel Biomarker for Sepsis", 64th Academic Meeting of Japanese Society of Laboratory Medicine, Oct. 20, 2017, vol. 65, supplement, p. 13. (4 pages).

Office Action (The First Office Action) issued Feb. 22, 2023, by the State Intellectual Property Office of People's Republic of China in corresponding Chinese Patent Application No. 201880080998.7. (9 pages).

\* cited by examiner

METHOD FOR DETERMINING BACTERIAL NUMBER IN SPECIMEN

TECHNICAL FIELD

The present invention relates to determining bacterial number in specimens, particularly in a blood specimen, by a PCR method or a method for rapidly and accurately determining bacterial number and species.

BACKGROUND ART

Clinical test items conventionally used for determining severity of sepsis include, e.g., blood culture, endotoxin, procalcitonin, white blood cell count, CRP (C-reactive protein), blood pressure, body temperature, respiratory rate and pulse rate. Recently, presepsin was newly added to these items. Since it takes time to obtain results by culturing blood, it is difficult to promptly feed back the results for treatment. White blood cell count and CRP are results of a defense reaction of a host against infection, there is a time lag between receipt of test values and progression into severe conditions, i.e., the disease condition indicated by the clinical test values often differs from actual severity. Procalcitonin has a drawback in specificity and quantitativeness. Due to the drawback, it is difficult to use procalcitonin. Presepsin cannot be applied to a patient with a kidney failure. As described, reliable test items indicating or reflecting severity and therapeutic effect of infectious diseases in real time have not yet been present. The bacterial number in a patient specimen, if it can be used as a biomarker, i.e., an index for determining the severity of an infectious disease and monitoring the therapeutic effect, will be the most direct and rational means.

Currently, the standard analysis for determining bacterial number in a specimen, which is performed by culturing a specimen taken from a patient; is nothing more than extremely rough quantification (only classified like "1+", "2+", "3+"). Culturing is a technique long been used; however, it takes long time (usually, 2 to 3 days) for examination. In addition, since proliferation ability varies depending on the bacterial species, the reliability of quantitative results using Colony-forming unit (CFU) is low. Accordingly, to obtain accurate bacterial number, a measuring method less dependent on culturing is preferably employed. Recent years, as the most available technology except culturing is a quantitative PCR (real-time PCR) method.

When the number of pathogenic bacterial cells of a patient's specimen is determined by the real-time PCR method, since the species of the pathogenic bacterium has not yet been identified in the beginning of examination and sometimes concomitant infection may occur, it is necessary to use a bacterial universal primer (primer that can detect almost all bacterial cells, hereinafter sometimes simply referred to as a "universal primer"). However, since a pathogenic bacterium is often present in a small amount in a patient specimen, the sensitivity of real-time PCR usually used is sometimes not sufficient for accurately determining the number of the pathogenic bacterial cells. Even if the real-time PCR is sufficiently sensitive, if bacterial universal PCR (PCR detecting almost all bacteria) is used, there is a problem: contamination is easily detected. Consequently, determination of a pathogenic bacterium becomes difficult. As a result, although the quantitative analysis of a pathogenic bacterium in a patient specimen is extremely useful for treating an infectious disease, the analysis has not yet been put in practical use because of the technical problem that remains unsolved.

As a method for identifying a pathogenic bacterium of an infectious disease according to a PCR method, Patent Literature 1 discloses a rapid identification method for a bacterial species causing an infection, in which a specimen-derived nucleic acid is subjected to a real-time PCR using a plurality of predetermined primer sets, and a pathogenic bacterium in the specimen is identified using a combination of melting temperatures (Tm values) of a plurality of amplification products obtained.

Patent Literature 2 discloses a method for identifying a bacterial species by a PCR method using a heat-resistant DNA polymerase, which is produced in a eukaryote and can achieve improvement of detection-sensitivity.

Patent Literature 3 discloses a large number of primer pairs for identifying bacteria in a specimen based on the melting temperature (Tm value) of an amplification product obtained by real-time PCR using a nucleic acid derived from a specimen.

CITATION LIST

Patent Literature

Patent Literature 1: International Publication No. WO2007/097323
Patent Literature 2: International Publication No. WO2010/082640
Patent Literature 3: International Publication No. WO2015/053293

SUMMARY OF INVENTION

Technical Problem

When the number and species of a pathogenic bacterium contained in an extremely small amount in a specimen such as a blood specimen of a patient with sepsis are analyzed by a conventional PCR method, the following problems still remain unsolved.

In conventional real-time PCR, the sensitivity is sometimes not sufficient to accurately determine the number of pathogenic bacterial cells in a patient specimen. Particularly, if the amount of a pathogenic bacterium is extremely low, the bacterium sometimes cannot be accurately determined by real-time PCR.

An object of the present invention is to provide a method for rapidly and accurately determining the number of bacterial cells in a specimen using a PCR method or a method for enabling determination of the cell number and species of a bacterium.

Solution to Problem

An embodiment of a first method for determining the number of bacterial cells in a specimen according to the present invention is characterized by having the following steps:

(1) a first PCR step of carrying out a PCR method using a nucleic acid derived from a specimen as a template and a universal primer pair for amplifying a bacterial 16S rRNA gene to obtain a first amplification product;
(2) a second PCR step of carrying out a nested PCR method using a primer pair(s) for amplifying an internal sequence(s) of the sequence of the first amplification product obtained by the first PCR step to obtain a second amplification product; and
(3) a bacterial number determination step of obtaining the number of bacterial cells in the specimen based on the amount of the second amplification product obtained in the second PCR step and using calibration data showing the relationship between the amount of the amplification product derived from a control bacterium of a known species and the cell number of the control bacterium.

An embodiment of a first method for determining the number of bacterial cells in a specimen according to the present invention is characterized by having the following steps:
(A) a first PCR step of carrying out a PCR method using a nucleic acid derived from a specimen as a template and a universal primer pair for amplifying a bacterial 16S rRNA gene to obtain a first amplification product;
(B) a second PCR step of carrying out a nested PCR method using a primer pair(s) for amplifying an internal sequence(s) of the sequence of the first amplification product obtained by the first PCR step to obtain a second amplification product;
(C) a third PCR step of carrying out a PCR method using a nucleic acid sample of a control bacterium of a known species and corresponding to the known number of bacterial cells and to obtain a third amplification product;
(D) a fourth PCR step of carrying out a nested PCR method using the third amplification product obtained by the third PCR step to obtain a fourth amplification product;
(E) a step of preparing calibration data based on the known number of bacterial cells and the amount of the fourth amplification product; and
(F) a bacterial number determination step of obtaining the number of bacterial cells in a specimen based on the amount of the second amplification product obtained in the second PCR step and using the calibration data.

An embodiment of a second method for determining the number of bacterial cells in a specimen according to the present invention is characterized by having the following steps:
(1) a first PCR step of carrying out a PCR method using a nucleic acid derived from a specimen as a template and a universal primer pair for amplifying a bacterial 16S rRNA gene to obtain a first amplification product;
(2) a second PCR step of carrying out a nested PCR method using a primer pair(s) for amplifying an internal sequence(s) of the sequence of the first amplification product obtained by the first PCR step to obtain a second amplification product;
(3) a bacterial number determination step of obtaining a provisional number of bacterial cells in a specimen based on the amount of a second amplification product obtained in the second PCR step and using calibration data showing the relationship between the amount of an amplification product derived from a control bacterium of a known species and the cell number of the control bacterium;
(4) a bacterial species identification step of identifying the species of a bacterium in the specimen; and
(5) a bacterial number correction step of correcting the provisional number of bacterial cells obtained in the bacterial number determination step based on the control bacterium and the 16S rRNA operon copy number of the bacterial species identified in the bacterial species identification step to determine the number of bacterial cells in the specimen.

An embodiment of a second method for determining the number of bacterial cells in a specimen according to the present invention is characterized by having the following steps:
(A) a first PCR step of carrying out a PCR method using a nucleic acid derived from a specimen as a template and a universal primer pair for amplifying a bacterial 16S rRNA gene to obtain a first amplification product;
(B) a second PCR step of carrying out a nested PCR method using a primer pair(s) for amplifying an internal sequence(s) of the sequence of the first amplification product obtained by the first PCR step to obtain a second amplification product;
(C) a third PCR step of carrying out a PCR method using nucleic acid sample of a control bacterium of a known species and corresponding to the known number of bacterial cells to obtain a third amplification product;
(D) a fourth PCR step of carrying out a nested PCR method using the third amplification product obtained by the third PCR step to obtain a fourth amplification product;
(E) a step of preparing calibration data based on the known number of cells of a control bacterium and the amount of the fourth amplification product;
(F) a bacterial number determination step of obtaining a provisional number of bacterial cells in a specimen based on the amount of the second amplification product obtained in the second PCR step and using the calibration data;
(G) a bacterial species identification step of identifying the species of a bacterium in the specimen; and
(H) a bacterial number correction step of correcting the provisional number of bacterial cells obtained in the bacterial number determination step based on the control bacterium and the 16S rRNA operon copy number of the bacterial species identified in the bacterial species identification step to determine the number of bacterial cells in the specimen.

A method for determining the presence or absence of contamination according to the present invention is characterized by having the following steps:
Step (a) of centrifuging a blood specimen to separate a red blood cell fraction, a buffy coat fraction and a plasma fraction, and then preparing sample A containing the plasma fraction of the supernatant and buffy coat, and sample B containing the plasma fraction of the supernatant and no buffy coat;
Step (b) of determining the number of bacterial cells of each of sample A and sample B by a method for determining the number of bacterial cells in a specimen and having the following steps (2-1), (2-2) and (2-3); and
Step (c) of determining the presence or absence of contamination of the bacterium in the blood specimen by comparing bacterial numbers of sample A and sample B;
(2-1) a first PCR step of carrying out a PCR method using a nucleic acid derived from a specimen as a template and a universal primer pair for amplifying a bacterial 16S rRNA gene to obtain a first amplification product;
(2-2) a second PCR step of carrying out a nested PCR method using a primer pair(s) for amplifying an internal sequence(s) of the sequence of the first amplification product obtained by the first PCR step to obtain a second amplification product; and (2-3) a bacterial number determination step of obtaining a provisional number of bacterial cells in a specimen based on the amount of the second amplification product obtained in the second PCR step and using the calibration data.

The step (b) of determining the number of bacterial cells in the method for determining the presence or absence of contamination according to the present invention may further have the following steps (2-4) and (2-5):

(2-4) a bacterial species identification step of identifying the species of a bacterium in the specimen; and (2-5) a bacterial number correction step of correcting the provisional number of bacterial cells obtained in the bacterial number determination step, based on the control bacterium and the 16S rRNA operon copy number of the bacterial species identified in the bacterial species identification step to determine the number of bacterial cells in the specimen.

Advantageous Effects of Invention

According to the present invention, it is possible to provide a method for enabling rapidquick and accurate determination of the number of bacterial cells in specimen using a PCR method or a method for enabling rapid and accurate determination of the number of bacterial cells and species of a bacterium in specimen using a PCR method.

DESCRIPTION OF EMBODIMENTS

Figure 1:
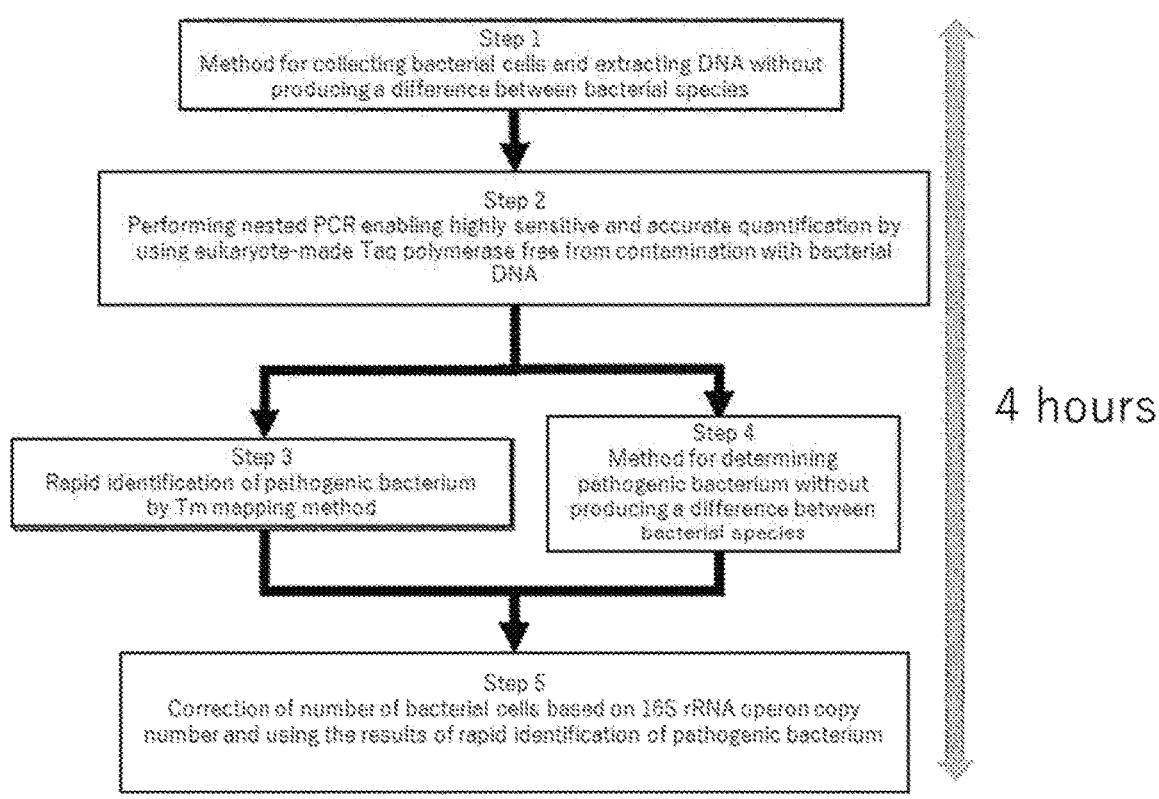
FIG. 1 The figure shows the relationship between individual steps in Example 1 and procedure thereof.

The first method for determining the number of bacterial cells in a specimen of the present invention has the following steps:

(i) a first PCR step of carrying out a PCR method using a nucleic acid derived from a specimen as a template and a universal primer pair for amplifying bacterial 16S rRNA gene to obtain a first amplification product;

(ii) a second PCR step of carrying out a nested PCR method using a primer pair(s) for amplifying an internal sequence(s) of the sequence of the first amplification product obtained by the first PCR step to obtain a second amplification product; and (iii) a bacterial number determination step of obtaining the number of bacterial cells in the specimen based on the amount of the second amplification product obtained in the second PCR step and using calibration data showing the relationship between the amount of the amplification product derived from a control bacterium of a known species and the cell number of the control bacterium.

The second method for determining the number of bacterial cells in a specimen of the present invention has the following steps:

(I) a first PCR step of carrying out a PCR method using a nucleic acid derived from a specimen as a template and a universal primer pair for amplifying a bacterial 16S rRNA gene to obtain a first amplification product;

(II) a second PCR step of carrying out a nested PCR method using a primer pair(s) for amplifying an internal sequence(s) of the sequence of the first amplification product obtained by the first PCR step to obtain a second amplification product;

(III) a bacterial number determination step of obtaining a provisional number of bacterial cells in a specimen based on the amount of a second amplification product obtained in the second PCR step and using calibration data showing the relationship between the amount of an amplification product derived from a control bacterium of a known species and the cell number of the control bacterium;

(IV) a bacterial species identification step of identifying the species of a bacterium in the specimen;

(V) a bacterial number correction step of correcting the provisional number of bacterial cells obtained in bacterial number determination step based on the control bacterium and the 16S rRNA operon copy number of the bacterial species identified in the bacterial species identification step to determine the number of bacterial cells in the specimen.

Now, an embodiment of the method for determining the number of bacterial cells in a specimen according to the present invention will be described below.

First, the first PCR step, second PCR step and bacterial number determination step, which are common in the first and second methods for determining the number of bacterial cells in a specimen according to the present invention, will be described.

(Preparation of Specimen-Derived Nucleic Acid Sample)

A nucleic acid sample derived from a specimen can be prepared according to a routine method.

Note that a nucleic acid sample derived from a specimen is preferably prepared by collecting bacteria so as not to produce a difference between bacterial species and extracting a nucleic acid according to the manner used in Examples (described later).

As the specimen, other than blood, e.g., cerebrospinal fluid (bacterial meningitis), pericardial effusion (pericarditis), pleural effusion (pleurisy), ascites (peritonitis), joint capsule fluid (orthopedic surgery postoperative infection), aqueous humor (endophthalmitis), alveolar lavage fluid (pneumonia), urine (urinary-tract infection), post-surgery drainage (postoperative infection) and CV catheter tip (sepsis of a long-term bedridden patient caused by catheter-tip Biofilm), which are possibly used as indexes for severity and therapeutic effect of various infectious diseases, and indexes for infectious disease risk management, can be mentioned.

(Primer Pair for First PCR)

The universal primer pair to be used in the first PCR step is not particularly limited as long as it can amplify a region available for quantifying 16S rRNA gene of a bacterial species, which is a target for quantification or which falls within a possible target range; and more specifically, a primer pair(s) known in the art and a primer pair(s) selected from base sequence information of bacterial 16S rRNA gene can be used.

In the case where the two base sequences of a 16S rRNA genes of different bacterial species, to which a primer is to be bound, differ in single base, if a primer to be bound to one of the two base sequences is used and a single-base mismatch occurs, quantification accuracy may decrease. In this case, it is preferable to use primers complementary to the two base sequences at the same time to enlarge the range of bacterial species enabling accurate quantification.

In other words, a universal primer pair for use in the first PCR step is preferably a mixture containing two types of forward primers and reverse primers, either one or both of which differ in single base, in equivalent amounts.

Examples of such a combination of the primer pairs are as follow:

Pattern 1:

```
Region 1 forward primer 1a:
                                       (SEQ ID No. 1)
5'-AGAGTTTGATCATGGCTCAG-3'

Region 1 forward primer 1b:
                                       (SEQ ID No. 2)
5'-AGAGTTTGATCCTGGCTCAG-3'

Region 7 reverse primer:
                                       (SEQ ID No. 3)
5'-CCGGGAACGTATTCACC-3'
```

In Pattern 1, it is preferable to mix Region 1 forward primers 1a and 1b in a quantitative ratio of 1:1 and put in use. A single primer, i.e., Region 7 reverse primer, is preferably used as it is. In the first PCR step, a single specimen per tube is preferably subjected to the PCR.

Pattern 2:

```
Region 1' forward primer 1a:
                                       (SEQ ID No. 1)
5'-AGAGTTTGATCATGGCTCAG-3'
```

```
Region 1' forward primer 1b:
                                       (SEQ ID No. 2)
5'-AGAGTTTGATCCTGGCTCAG-3'

Region 7' reverse primer 1a:
                                       (SEQ ID No. 4)
5'-AGACCCGGGAACGTATTC-3'

Region 7' reverse primer 1b:
                                       (SEQ ID No. 5)
5'-AGGCCCGGGAACGTATTC-3'
```

In Pattern 2, it is preferable to mix Region 1' forward primers 1a and 1b in a quantitative ratio of 1:1 and put in use. Similarly, it is preferable to mix Region 7' reverse primers 1a and 1b in a quantitative ratio of 1:1 and put in use. In the first PCR step, a single specimen per tube is preferably subjected to the PCR.

(First PCR Step)

In the first PCR step, in order to obtain the amount of an amplification product corresponding to the amount of a nucleic acid used as a template for improving accuracy in quantification, it is preferable to terminate amplification before gene amplification reaches a plateau, for example, at a (linear) portion with a slope of the amplification curve. The amplification rate of an amplification product can be controlled by, e.g., concentration of PCR reagents, activity of an enzyme for PCR and the number of amplification cycles. The number of cycles before gene amplification reaches a plateau is determined based on estimation from the amount of a nucleic acid contained in a nucleic acid sample or based on data experimentally obtained in advance and the amplification rate is controlled. In this manner, it is preferable to terminate PCR before gene amplification reaches a plateau.

The first PCR step can be carried out by a method and apparatus known in the art.

The first PCR step is preferably carried out in a reaction system extremely less or not contaminated with bacteria-derived nucleic acids except a specimen-derived nucleic acid. Such a reaction system can be prepared by treating PCR reagents, experimental instruments and enzymes in manners known in the art as disclosed in Patent Literature 2. As the enzyme for amplifying a nucleic acid, heat-resistant DNA polymerase is preferably used, which is produced by a genetic engineering procedure using a eukaryote disclosed in Patent Literature 2 as a host. If PCR is carried out without contamination with bacteria-derived nucleic acids except a specimen-derived nucleic acid, background due to amplification of contaminant bacteria-derived nucleic acids becomes zero or a detection limit or less, with the result that the number of pathogenic bacterial cells, even if it is extremely small, can be accurately determined.

(Primer Pair for Second PCR)

A second PCR step is carried out according to a nested PCR method using the amplification product obtained in the first PCR step.

As the primer pair for the second PCR step is not particularly limited as long as it can amplify a nucleic acid fragment having an internal sequence(s) of a base sequence of the amplification product obtained in the first PCR step and available for determination of the cell number of a desired bacterium. A primer pair(s) known in the art or a primer pair(s) selected from the base sequence of bacterial 16S rRNA gene can be used.

As the preferable primer pair for the second PCR step, the following primer pairs can be mentioned.

Pattern 1:

```
Region 1 forward primer:
                              (SEQ ID No. 1)
5'-AGAGTTTGATCATGGCTCAG-3'

Region 1 reverse primer:
                              (SEQ ID No. 6)
5'-CGTAGGAGTCTGGACCGT-3'

Region 2 forward primer:
                              (SEQ ID No. 7)
5'-GACTCCTACGGGAGGCA-3'

Region 2 reverse primer:
                              (SEQ ID No. 8)
5'-TATTACCGCGGCTGCTG-3'

Region 3 forward primer:
                              (SEQ ID No. 9)
5'-AGCAGCCGCGGTAATA-3'

Region 3 reverse primer:
                              (SEQ ID No. 10)
5'-GGACTACCAGGGTATCTAATCCT-3'

Region 4 forward primer:
                              (SEQ ID No. 11)
5'-AACAGGATTAGATACCCTGGTAG-3'

Region 4 reverse primer:
                              (SEQ ID No. 12)
5'-AATTAAACCACATGCTCCACC-3'

Region 5 forward primer:
                              (SEQ ID No. 13)
5'-TGGTTTAATTCGATGCAACGC-3'

Region 5 reverse primer:
                              (SEQ ID No. 14)
5'-GAGCTGACGACAGCCAT-3'

Region 6 forward primer:
                              (SEQ ID No. 15)
5'-TTGGGTTAAGTCCCGC-3'

Region 6 reverse primer:
                              (SEQ ID No. 16)
5'-CGTCATCCCCACCTTC-3'

Region 7 forward primer:
                              (SEQ ID No. 17)
5'-GGCTACACACGTGCTACAAT-3'

Region 7 reverse primer:
                              (SEQ ID No. 3)
5'-CCGGGAACGTATTCACC-3'

Pattern 2:
Region 1' forward primer:
                              (SEQ ID No. 18)
5'-GCAGGCTTAACACATGCAAGTCG-3'

Region 1' reverse primer:
                              (SEQ ID No. 6)
5'-CGTAGGAGTCTGGACCGT-3'

Region 2' forward primer:
                              (SEQ ID No. 19)
5'-GTCCAGACTCCTACGGGAG-3'

Region 2' reverse primer:
                              (SEQ ID No. 20)
5'-CCTACGTATTACCGCGG-3'

Region 3' forward primer:
                              (SEQ ID No. 21)
5'-AGCAGCCGCGGTAATA-3'

Region 3' reverse primer:
                              (SEQ ID No. 10)
5'-GGACTACCAGGGTATCTAATCCT-3'

Region 4' forward primer:
                              (SEQ ID No. 11)
5'-AACAGGATTAGATACCCTGGTAG-3'

Region 4' reverse primer:
                              (SEQ ID No. 12)
5'-AATTAAACCACATGCTCCACC-3'

Region 5' forward primer:
                              (SEQ ID No. 13)
5'-TGGTTTAATTCGATGCAACGC-3'

Region 5' reverse primer:
                              (SEQ ID No. 14)
5'-GAGCTGACGACAGCCAT-3'

Region 6' forward primer:
                              (SEQ ID No. 22)
5'-GTTAAGTCCCGCAACGAG-3'

Region 6' reverse primer:
                              (SEQ ID No. 23)
5'-CCATTGTAGCACGTGTGTAGCC-3'

Region 7' forward primer:
                              (SEQ ID No. 24)
5'-GGCTACACACGTGCTACAATGG-3'

Region 7' reverse primer:
                              (SEQ ID No. 4)
5'-AGACCCGGGAACGTATTC-3'
```

The second PCR step can be carried out using at least one primer pair selected from the group consisting of patterns 1 and 2. Note that, if a plurality of primer pairs are used, the second PCR step is carried out using these separately.

(Second PCR Step)

The second PCR step can be carried out by a method and apparatus known in the art.

Note that, the reaction solution containing the amplification product obtained in the first PCR step may be diluted, if necessary, in obtaining the amount of the amplification product enough to be used for quantification in the second PCR step.

The dilution rate is determined such that an amplification product can be obtained in the second PCR step in an amount estimated from the concentration of the amplification product in reaction solution obtained in the first PCR step, or in an amount falling within the range of ensuring quantitativeness in an experiment performed in advance.

Also, the second PCR step is preferably carried out in a reaction system extremely less or not contaminated with bacteria-derived nucleic acids except a specimen-derived nucleic acid. Such a reaction system can be prepared by treating PCR reagents, experimental instruments and enzymes in manners known in the art as disclosed in Patent Literature 2. As the enzyme for amplifying a nucleic acid, heat-resistant DNA polymerase is preferably used, which is produced by a genetic engineering procedure using a eukaryote disclosed in Patent Literature 2 as a host. If PCR is carried out without contamination with bacteria-derived nucleic acids except a specimen-derived nucleic acid, background due to amplification of contaminant bacteria-derived nucleic acids becomes zero or a detection limit or less, with the result that the number of pathogenic bacterial cells, even if it is extremely small, can be accurately determined.

(Preparation of Calibration Data)

In bacterial number determination step, the number of bacterial cells in a specimen can be determined using calibration data showing the relationship between the amount of the amplification product from a control bacterium of a known species and the number of bacterial cells serving as a control bacterium.

Although it cannot be particularly limited, the calibration data can be prepared, based on the relationship between the amount of an amplification product derived from a bacterium of a known species, (which is obtained by carrying out a PCR step using a nucleic acid sample of a control bacterium of a known species and corresponding to the known number of bacterial cells) and the known number of bacterial cells of a known species. The calibration data can be prepared using the known number of control bacterial cells alone or individually using different known bacterial numbers of a control bacterium.

Although it cannot be particularly limited, the calibration curve if it is used in place of the calibration data, can be prepared based on the relationship between the amount of an amplification product derived from a bacterium of a known species (which is obtained by carrying out a PCR step each independently using a plurality of nucleic acid samples of a control bacterium of a known species and corresponding to a plurality of different known numbers of bacterial cells) and the known number of bacterial cells of a known species.

The calibration data are prepared in advance and used in bacterial number determination step.

In order to improve accuracy in determination of number of bacterial cells by reducing errors due to operation condition and environment of a PCR apparatus to a minimum, it is preferable to prepare calibration data by the first PCR step and second PCR step in series. In this case, calibration data can be prepared by the following steps:

(C) a third PCR step of carrying out a PCR method using a nucleic acid sample of a control bacterium of a known species and corresponding to the known number of bacterial cells to obtain a third amplification product;

(D) a fourth PCR step of carrying out a nested PCR method using the third amplification product obtained by the third PCR step to obtain a fourth amplification product; and (E) a step of preparing calibration data based on the known number of cells of a control bacterium and the amount of the fourth amplification product.

Note that, calibration data can be efficiently prepared by carrying out the first PCR step and the third PCR step concurrently in the same PCR apparatus, and the second PCR step and the fourth PCR step concurrently in the same PCR apparatus.

If a calibration curve is used as calibration data, the following steps (C-1) and (E-1) can be employed in place of step (C) and (E):

(C-1) a third PCR step of carrying out a PCR method independently using each of a plurality of nucleic acid samples of a control bacterium of a known species and corresponding to a plurality of different known numbers of bacterial cells to obtain a third amplification product; and (E-1) a step of preparing a calibration curve based on the known number of bacterial cells and the amount of the fourth amplification product.

As a plurality of nucleic acid samples used as templates in the third PCR step for preparing a calibration curve, samples obtained by extracting nucleic acids respectively from a plurality of samples containing a different known cell number of control bacterium, can be used. Alternatively, the nucleic acid sample, which is obtained by extracting a nucleic acid from a sample containing a known number of control bacterial cells, is diluted up to a predetermined concentration to prepare a plurality of nucleic acid samples corresponding to a plurality of different known numbers of control bacterial cells. The nucleic acid samples thus obtained may be each independently used in the third PCR step.

The control bacterium is not particularly limited as long as a desired calibration curve can be prepared. The control bacterium can be selected in consideration of, e.g., handleability and interchangeability with other bacterial species. In view of this, *Escherichia coli* can be preferably used as the control bacterium.

The primer set to be used for preparing a calibration curve is preferably selected in consideration of relationship among the first PCR step, second PCR step and the primer set for a PCR step if the PCR is used for identifying species of a bacterium in a specimen (described later). For example, if the primer set to be used in the first PCR step can be used in step (C) and the primer set (at least one primer set if a plurality of primer sets are used) to be used in the second PCR step can be used in step (D). Also in a case (described later) of using the amplification product in the first PCR step for identifying species of a bacterium in a specimen, the primer set (at least one primer set if a plurality of primer sets are used) to be used in the second PCR step can be used in step (D), similarly.

(Calculation of Bacterial Number)

In the bacterial number determination step, the number of bacterial cells in a specimen can be obtained based on the amount of an amplification product obtained in the second PCR step and using calibration data such as a calibration curve. The number of bacterial cells can be used as the number of bacterial cells in a specimen.

Note that, in the second method for determining the number of bacterial cells according to the present invention, the number of bacterial cells obtained in the bacterial number determination step is used as a provisional number of bacterial cells (provisionally determined).

Now, the bacterial species identification step and bacterial number correction step in the second method for determining the number of bacterial cells according to the present invention will be described below. Note that a bacterial species identification step may be added to the first method for determining the number of bacterial cells according to the present invention. In this case, using the first PCR step and second PCR step in the first method for determining the number of bacterial cells, a bacterium in a specimen can be identified.

(Primers for Identifying Bacterial Species)

In the second method for determining the number of bacterial cells according to the present invention, the species of a bacterium in a specimen is determined using the amplification product obtained in the first PCR step.

When the primer set of pattern 1 is used for identifying a bacterial species by the Tm mapping method (described later), it is preferable to use the following primer set.

First PCR step (the same as the primer set of the first PCR step of pattern 1 of Tm mapping method)

Region 1 forward primers 1a and 1b are mixed in a quantitative ratio of 1:1 and put in use. A single primer, i.e., Region 7 reverse primer, is preferably used as it is. As patient's specimen for 1st PCR, a single specimen per tube is used. As a quantification control, at least one single concentration thereof per tube is used; more preferably, three concentrations thereof in 3 tubes are used. As the negative control, a single tube is used.

```
Region 1 forward primer 1a:
                                    (SEQ ID No. 1)
5'-AGAGTTTGATCATGGCTCAG-3'

Region 1 forward primer 1b:
                                    (SEQ ID No. 2)
5'-AGAGTTTGATCCTGGCTCAG-3'

Region 7 reverse primer:
                                    (SEQ ID No. 3)
5'-CCGGGAACGTATTCACC-3'
```

Second PCR step (nested PCR):

The following Region 3 forward primer and Region 3 reverse primer are used. The quantification in the 2nd nested PCR is carried out using a single specimen per tube; at least one concentration of quantification control in a single tube, more preferably, 3 concentrations thereof in 3 tubes; and a single negative control tube. Note that, in the case of a patient specimen, amplification results by Region 3 forward & reverse primer by Tm mapping method are directly used in quantitative measurement (PCR needs not be carried out using a new tube for quantification).

```
Region 3 forward primer:
                                    (SEQ ID No. 9)
5'-AGCAGCCGCGGTAATA-3'

Region 3 reverse primer:
                                    (SEQ ID No. 10)
5'-GGACTACCAGGGTATCTAATCCT-3'
```

If Tm mapping method using the primer set of pattern 2 is used for identification of bacterial species, the following primer sets are preferably used.

First PCR step (the same as the primer set of the first PCR step of pattern 2 of Tm mapping method)

The following Region 1' forward primers 1a and 1b are mixed in a quantitative ratio of 1:1 and put in use. Similarly, Region 7' reverse primers 1a and 1b are mixed in a quantitative ratio of 1:1 and put in use. A single PCR specimen per tube is used. As a quantification control, at least one single concentration thereof per tube is used; more preferably, three concentrations thereof in 3 tubes are used. As the negative control, a single tube is used.

```
Region 1' forward primer 1a:
                                    (SEQ ID No. 1)
5'-AGAGTTTGATCATGGCTCAG-3'

Region 1' forward primer 1b:
                                    (SEQ ID No. 2)
5'-AGAGTTTGATCCTGGCTCAG-3'

Region 7' reverse primer 1a:
                                    (SEQ ID No. 4)
5'-AGACCCGGGAACGTATTC-3'

Region 7' reverse primer 1b:
                                    (SEQ ID No. 5)
5'-AGGCCCGGGAACGTATTC-3'
```

Second PCR step (nested PCR):

Region 3' forward primer and Region 3' reverse primer are used. The quantification in the 2nd nested PCR is carried out using a single specimen per tube, at least one concentration of quantification control in a single tube, more preferably, 3 concentrations thereof in 3 tubes; and a single negative control tube. Note that, in the case of a specimen, amplification results by Region 3' forward & reverse primer by Tm mapping method are directly used in quantitative measurement (PCR needs not be carried out using a new tube for quantification).

```
Region 3' forward primer:
                                    (SEQ ID No. 9)
5'-AGCAGCCGCGGTAATA-3'

Region 3' reverse primer:
                                    (SEQ ID No. 10)
5'-GGACTACCAGGGTATCTAATCCT-3'
```

Note that the number of quantification controls in individual PCR steps is not particularly limited. A single tube or two or more tubes of quantification controls different in concentration may be used.

(Identification of Bacterial Species in Specimen)

Bacterial species can be identified by a method known in the art, for example, disclosed in Patent Literatures 1 to 3.

For example, a method for identifying a bacterial species by detecting the presence or absence of an amplification product specific to the bacterial species, can be used. For detecting the presence or absence of an amplification product specific to the bacterial species, the following method can be used.

Method of confirming the presence or absence of an amplification product by real-time PCR using an intercalator or a probe having a fluorescent label for detection.

Method of measuring the Tm value of an amplification product by real-time PCR using an intercalator or a probe having a fluorescent label for detection.

Method for analyzing an amplification product by developing the amplification product by electrophoresis on, e.g., a gel and visualizing it.

Method for analyzing an amplification product by sequence analysis of the amplification product.

Method for analyzing an amplification product by measuring the molecular weight thereof by a mass spectrometer.

In addition, bacterial species can be identified by carrying out PCR using a plurality of primer pairs and measuring Tm values of a plurality of amplification products obtained.

As the method using a plurality of primer pairs, a nested PCR method using pattern 1 and pattern 2 primer sets described in the second PCR step, is preferably used.

It is preferable that a pathogenic bacterium is rapidly identified by carrying out PCR using Region 1 to 7 forward and reverse primer sets or a Region 1' to 7' forward and reverse primer sets (each primer set is placed in a single tube, 7 tubes in total per specimen), and carrying out Tm mapping method using the 7 Tm values obtained according to the method disclosed in Patent Literature 1.

Bacterial species can be identified by the Tm mapping method disclosed in, for example, Patent Literature 1, Patent Literature 2 (paragraph [0237]) or Patent Literature 3 (paragraphs [0111] to [0116]) or by appropriately modifying each of the methods disclosed in these literatures. In the identification of bacterial species by the Tm mapping method, identification data pertaining to a combination of Tm values of a plurality of amplification products (amplified by a plurality of predetermined primer pairs obtained from known bacterial species) or a combination of differences between a plurality of Tm values, are used. A combination of Tm values of a plurality of amplification products obtained using the same primer pairs from unknown bacterial samples (collected from specimens) or a combination of differences between Tm values is compared to the identification database. Based on degree of coincidence, the unknown bacteria in the specimens are identified.

The identification method is more specifically described by way of example, below.

<Identification Method>

To identify a bacterium detected, it is possible to use the Tm value of a DNA fragment, which is obtained from the bacterium detected using a primer set according to the present invention. A bacterium of an unknown species in a specimen can be identified by obtaining a DNA fragment and a Tm value thereof in advance using 16S rRNA or 16S rDNA of a plurality of bacteria, which are possibly contained particularly in a specimen, according to a method partly or wholly identical with the method of the invention; and using the Tm values or "relative values of Tm values" (described later) as comparison data or database. As the algorithm for use in identification, not only a combination of Tm values described above but also a combination of differences between Tm values is used. In this manner, an effect of a measurement error such as measurement error produced every time an apparatus is operated can be reduced to a minimum.

As a method for correcting a measurement error produced every time an apparatus is operated, a method of calculating "an average value of a combination of Tm values" and using a "combination of relative values" of individual Tm values obtained from the average value, can be used. More specifically, this is a method of identifying the arrangement of combinations of Tm values as "pattern". The two-dimensionally expressed "pattern" of the arrangement of combinations of Tm values is not influenced by measurement error. For example, combinations of Tm values specific to the detected bacterium (n combinations (n represents an integer of, for example, 4 or more and 7 or less)) are represented by T1db to Tndb (db stands for database) and relative values of the average value thereof are represented by d1db to dndb, respectively. Similarly, combinations (n combinations (n represents an integer of, for example, 4 or more and 7 or less)) of Tm values of an unknown detection-target organism obtained from a specimen are represented by T1ref to Tnref (ref stands for reference) and relative values of the average value thereof are represented by d1ref to dnref, respectively. In this way, comparison is carried out with the database, "a combination approximate to a combination of relative values=pattern close to the "pattern" of arrangement of combination of Tm values" is used as an identification algorithm.

As a specific calculation method, for example, a method of calculating a point-to-point distance of the Euclidean space (Expression 1) is mentioned; however, the calculation method is not limited to this.

$$\text{Dist.} = \sqrt{[(d1_{db}-d1_{ref})^2 + (d2_{db}-d2_{ref})^2 + \ldots (dn_{db}-dn_{ref})^2]}$$ [Expression 1]

If the method of calculation according to Expression 1 is employed, a bacterium whose Dist. value (obtained by the Expression) is the closest to 0 (zero) is identified as the bacterial species detected. However, Dist. value varies depending on the measurement error of the PCR apparatus used, more specifically varies depending on the spec of temperature control of the apparatus and the number of primers. The acceptable range of the Dist. value is 0 to 0.37 and preferably 0 to 0.30.

The algorithm mentioned above can be used as database-type identification software on computer.

<Identifiable Bacterial Species>

The species of an identifiable microorganism, as long as the microorganism falls within the range of taxonomic bacteria, can be mechanically detected and identified.

The number of primer pairs and the base sequences of the primer pairs can be selected according to, e.g., the detection range of bacterial species.

Note that, as the nucleic acid sample to be used in nested PCR, the amplification product obtained in the first PCR step is diluted, if necessary, and put in use. As the primer set herein, a combination of pattern 1 primer set for the first PCR step and pattern 1 primer set for the second PCR step and a combination of pattern 2 primer set for the first PCR step and pattern 2 primer set for the second PCR step are preferably used.

(Correction of Provisional Bacterial Number)

When the number of pathogenic bacterial cells contained in a small amount in a specimen such as a blood specimen of a patient with sepsis is analyzed by the first quantification method according to the present invention, the quantification result, which is obtained by determining the number of pathogenic bacterial cells by bacterial universal PCR, is a converted value to quantification-control bacterial species equivalent and often differs from the real number of pathogenic bacterial cells.

In the second quantification method according to the present invention, if the results of identification of bacterium in a specimen show that the bacterium contained in a specimen is the same species as a control bacterium, the provisional number of bacterial cells (previously obtained) is determined as the quantitative result. In contrast, if the results of identification of bacterium in a specimen show that the bacterium contained in a specimen is a different species from the control bacterium, the provisional number of bacterial cells is corrected based on the ratio of 16S ribosomal RNA operon copy number of the identified bacterium and 16S ribosomal RNA operon copy number of the control bacterium and the corrected value is determined as a quantitative result.

(Identification and Quantitation Kit)

Using, e.g., at least one of the primer sets mentioned above, the database to be used for identification by the Tm mapping method, heat resistant DNA polymerase not contaminated with bacterial DNA, a positive control and a negative control, a kit for quantification of bacteria in a specimen or a kit for identification/quantification of bacteria in a specimen, can be produced.

(Method for Determining the Presence or Absence of Contamination)

When the number of bacterial cells in a blood specimen is determined or when the number and species of bacterial cells in a blood specimen are both determined, if the blood specimen is contaminated with bacteria except those derived from the specimen in the period from sampling of a specimen to first or second PCR step, the accuracy in desired determination of the bacterial number/species including false positive results, often decreases. Because of this, the presence or absence of contamination of a PCR sample with bacteria except those derived from the specimen is previously checked. In this manner, reliability of determination of the desired bacterial number/species can be more improved.

A method for determining the presence or absence of contamination according to the present invention is characterized by having:

Step (1) of centrifuging a blood specimen to separate a red blood cell fraction, a buffy coat fraction and a plasma fraction to prepare sample A, which contains the plasma fraction of the supernatant and buffy coat, and sample B, which contains the plasma fraction of the supernatant and no buffy coat;

Step (2) of individually determining the number of bacterial cells of sample A and sample B according to the method of determining the number of bacterial cells in a specimen having the following steps (2-1), (2-2) and (2-3); and Step (3) of determining the presence or absence of contamination of the blood specimen with bacteria by comparing the bacterial numbers of sample A and sample B;

(2-1) a first PCR step of carrying out a PCR method using a nucleic acid derived from a specimen as a template and a universal primer pair for amplifying a bacterial 16S rRNA gene to obtain a first amplification product;

(2-2) a second PCR step of carrying out a nested PCR method using a primer pair(s) for amplifying an internal sequence(s) of the sequence of the first amplification product obtained by the first PCR step to obtain a second amplification product; and (2-3) a bacterial number determination step of obtaining the provisional number of bacterial cells in the specimen based on the amount of a second amplification product obtained in the second PCR step and using calibration data.

Steps (2-1) to (2-3) can be carried out by the first quantification method according to the present invention.

The step (b) of determining bacterial number may further have the following steps (2-4) and (2-5):

(2-4) a bacterial species identification step of identifying the species of a bacterium in the specimen; and (2-5) a bacterial number correction step of correcting the provisional number of bacterial cells obtained in bacterial number determination step based on the control bacterium and the 16S rRNA operon copy number of the bacterial species identified in the bacterial species identification step to determine the number of bacterial cells in the specimen.

Step (2-1) to step (2-5) can be carried out by the second quantification method according to the present invention.

A blood specimen is centrifuged to separate a red blood cell fraction, a buffy coat (white blood cell) fraction and a plasma fraction in this order from the lower layer toward the upper layer, according to the specific gravities of the components contained in the blood.

If the bacterial numbers of a sample containing a plasma fraction alone (without buffy coat) and a sample containing a plasma fraction and buffy coat (with buffy coat) are obtained by the quantitation method according to the present invention and compared, the presence or absence of contamination of the blood sample with bacteria except those derived from the specimen can be determined.

The sample "with buffy coat" contains white blood cells which ingest a pathogenic bacterium by phagocytosis in a patient's body; whereas, the sample "without buffy coat" contains only the plasma containing no white blood cells which ingest a pathogenic bacterium by phagocytosis. In the case that a patient and patient's specimen are not actually infected, and bacterial DNA derived from the skin-resident bacteria at the time of blood sampling, work environment and contamination of instruments is detected, these bacteria are not ingested by phagocytosis by white blood cells, meaning that no difference is present in bacterial number by the presence or absence of buffy coat. In contrast, if the bacterium detected is a pathogenic bacterium, the bacterium is ingested by phagocytosis by white blood cells in the patient's blood, with the result that number of bacterial cells should be markedly large in the sample "with buffy coat" compared to the sample "without buffy coat". In other words, the following determination can be made.

First, if bacteria are not present in a blood specimen, the bacterial cells are not counted in the sample "without buffy coat" or the sample "with buffy coat".

If bacteria are not present in a blood specimen and the blood sample is contaminated with bacteria except those derived from the specimen, the contaminant bacteria are not ingested by white blood cells by phagocytosis, with the result that the bacterial number does not differ between the two samples depending on the presence or absence of buffy coat. The "no difference in bacterial number" is an indicator showing that contamination with bacteria except those derived from the specimen occurs. It is less reliable to determine that the bacterium identified at this time is a pathogenic bacterium and also less reliable that the bacterial number reflects the actual number of bacterial cells in the blood.

If blood samples, which are derived from an infectious patient, contain a bacterium and are not contaminated with bacteria except those derived from the specimen, containing buffy coat and containing no buffy coat, are compared, and the bacterial number of the sample with buffy coat is large. Since the bacterial numbers differs in this case, the resultant bacterial numbers are highly reliably determined to reflect the actual numbers of bacterial cells in the blood; at the same time, the bacterium identified herein is highly reliably identified as a pathogenic bacterium.

If blood specimens, which are derived from an infectious patient, contain a bacterium and are contaminated with bacteria except those derived from the specimen, containing buffy coat and containing no buffy coat, are compared, and an apparent bacterial number of the sample with buffy coat is higher. Particularly, if the sample without buffy coat alone is contaminated with bacteria except those derived from the specimen during treatment, difference in bacterial number becomes low. If the bacterial mass in the blood due to infection is extremely low and if the mass of contaminant bacteria is extremely large, the difference in bacterial number between a sample without buffy coat and a sample with buffy coat becomes low. In contrast, if the bacteria mass in the blood due to infection is extremely large and if the mass of contaminant bacteria is extremely small, the difference in bacterial number between a sample without buffy coat and a sample with buffy coat becomes large. As just described, depending on the large or small of bacterial number, possibility of contamination into blood sample with bacteria except those derived from the specimen can be determined. The results obtained in the case where the difference in bacterial number is sufficiently large are highly reliable; whereas the results obtained in the case where the difference in bacterial number is small, are less reliable.

In step (c) of determining the presence or absence of contamination, how many bacterial cells can be detected in a basically bacteria-free specimen due to contamination derived from laboratory instruments and work environment and e.g., quantitative error by real-time PCR, must be checked (in advance); in other words, it is preferable to determine the presence or absence of contamination based on the difference in bacterial number between a sample without buffy coat and a sample with buffy coat, in consideration of the error range in actual measurement. The error range in this case is preferably determined by carrying out a test using, e.g., contamination-free sterile water as a negative control, using instruments actually used under working environment in a plurality of times within the range of the common technical knowledge of those skilled in the art, as shown in Example 3 (described later). In the ideal environment having no contamination and no real-time PCR errors, the error range is ±0 cells/ml. The range of ±100 cells/ml shown in Example 3 is tentatively used as a reference value.

Note that, in the step of determining the presence or absence of contamination, comparison may be made based on Ct (Threshold cycle) value obtained in real-time PCR, in addition to the comparison based on bacterial number, which is obtained by processing the result of real-time PCR at each test district into a numeric value based on a calibration curve obtained from the results of a quantification control.

According to the method of the present invention, the number of bacterial cells in a specimen can be highly accurately determined compared to a conventional biochemical property analysis.

Although determination of bacterial number generally takes about two days after blood sampling in a conventional biochemical property analysis, rapid determination as short as about 3.5 hours after blood sampling can be realized.

In the conventional biochemical property analysis, there are cases where a bacterial species cannot be identified and where a bacterium cannot be cultured depending on the species. In contrast, according to the method of the present invention, bacterial number determination can be made as long as the bacterial species has 16S rRNA gene sequence registered in the database and 16S rRNA operon copy number is known.

Although, in the conventional biochemical property analysis, it generally takes about one week to determine a sample as being negative; whereas, in the method according to the present invention, determination can be made as quick as about 3.5 hours after blood sampling.

Further, to the case where the number of bacterial cells in a specimen is used as a new indicator of determining severity of an infectious disease, the case where time-dependent change of the number of bacterial cells in a specimen serves as a new indicator of exhibiting a therapeutic effect, the case where reducing the bacterial number toward zero serves as an indicator of terminating administration of an antibacterial drug and the case where sepsis is defined based on the bacterial number as an index, an extremely useful technique for determining the number of bacterial cells in the specimen according to the present invention can be applied.

Further, in the case where the number and species of bacterial cells in a specimen are concurrently determined, the same effect as the above can be obtained.

EXAMPLES

Now, the present invention will be more specifically described by way of Examples. Note that, unless otherwise specified, PCR and treatments were carried out using reagents and instruments known in the art and a commercially available PCR apparatus according to routine manners.

Example 1

The connection between individual steps of Example 1 and the procedure thereof are shown in FIG. 1.

(Step 1: Method for Collecting Bacterial Cells and Extracting DNA without Producing a Difference Between Bacterial Species)

First, bacterial cells were collected from a blood specimen by centrifuging the whole blood at a low rate of 100×g for 5 minutes to separate blood cells, centrifuging the resultant supernatant (containing buffy coat) at a high rate of 20,000×g for 10 minutes to obtain a pellet. In this step, fractionation of bacteria in the plasma does not change and the efficiency in collecting bacterial cells does not differ depending on the bacterial species.

To confirm this, *Escherichia coli* (*E. coli* ATCC25922), *Staphylococcus aureus* (*S. aureus* ATCC29213), *Klebsiella pneumoniae* (*K. pneumoniae* NBRC3512) and *Pseudomonas aeruginosa* (*P. aeruginosa* ATCC27853) were separately dissolved in saline and centrifuged at a low rate of 100×g for 5 minutes. The upper half and the lower half of a liquid containing bacterial cells in the centrifuge tubes were separately poured in culture mediums and CFU was determined.

Note that, *Escherichia coli* (*E. coli* ATCC25922), *Staphylococcus aureus* (*S. aureus* ATCC29213) and *Pseudomonas aeruginosa* (*P. aeruginosa* ATCC27853) are available from American Type Culture Collection (10801 University Boulevard, Manassas (Va.), 20110-2209 USA). *Klebsiella pneumoniae* (*K. pneumoniae* NBRC3512) is available from the National Institute of Technology And Evaluation (NITE) Biotechnology Center (NBRC) (address: 2-5-8, Kazusaka-matari, Kisarazu-shi, Chiba 292-0818 Japan).

Figure 2:
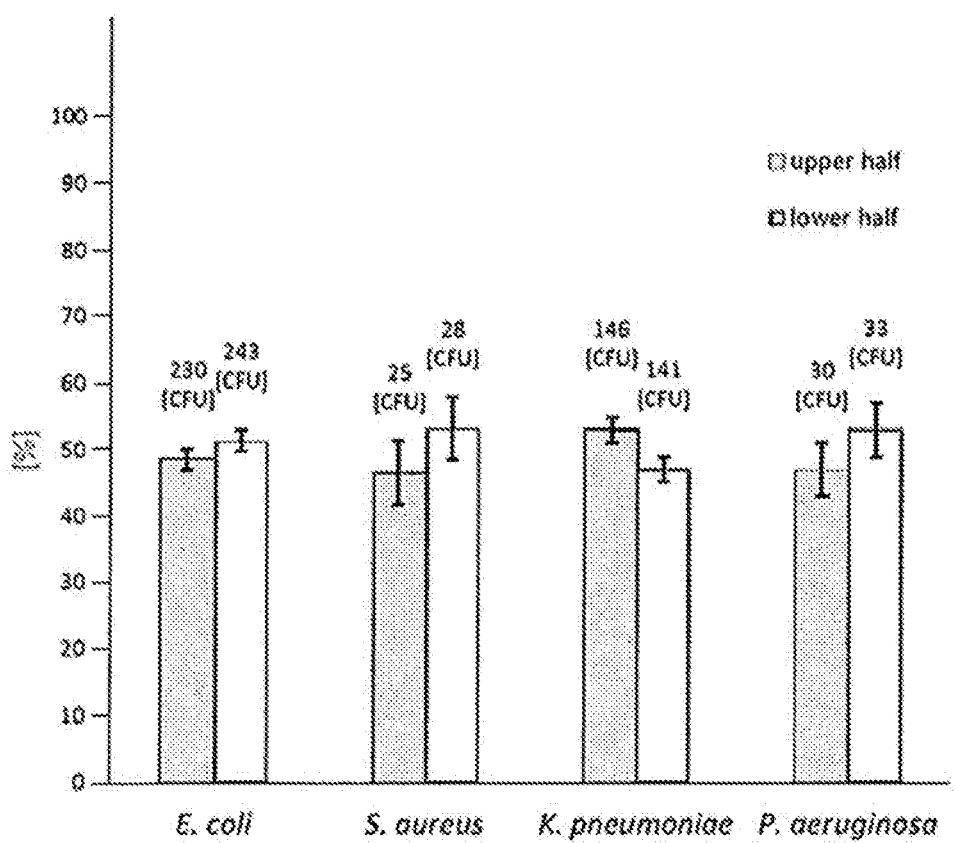
FIG. 2 The figure is a graph showing the number of bacterial cells in the upper half and lower half of each of the liquid obtained by centrifuging bacterial dispersions at a low rate of 100×g for 5 minutes.

The results are shown in FIG. 2. From the results, no difference was found in the bacterial number of the upper half and lower half after centrifugation. In other words, the efficiency in collecting bacteria cells of these species do not vary depending on the centrifugation conditions.

For DNA extraction, bacterial cells collected were treated with a protease and physically crushed with beads. In this manner, bacterial cell walls were completely destroyed so as not to produce difference in DNA extraction efficiency between bacterial species.

(Step 2: Nested PCR Enabling Highly Sensitive and Accurate Quantification Using Heat Resistant DNA Polymerase not Contaminated with Bacterial DNA)

Using DNA of a pathogenic bacterium taken from the blood specimen according to the method of Step 1 as a template, nested PCR (1st PCR: 30 cycle→100 double dilution→2nd PCR: 30 to 35 cycles) is carried out. The bacterial cells in patient specimens vary in a wide range from very small to large number. Since it is difficult to accurately determine the bacterial number in a single cycle of PCR, nested PCR methods are used in combination. Note that, nested PCR is desirably carried out in such conditions that gene amplification does not reach a plateau by the 1st PCR, more specifically, the cycle of 1st PCR is repeated 30 times or less.

Figure 3:
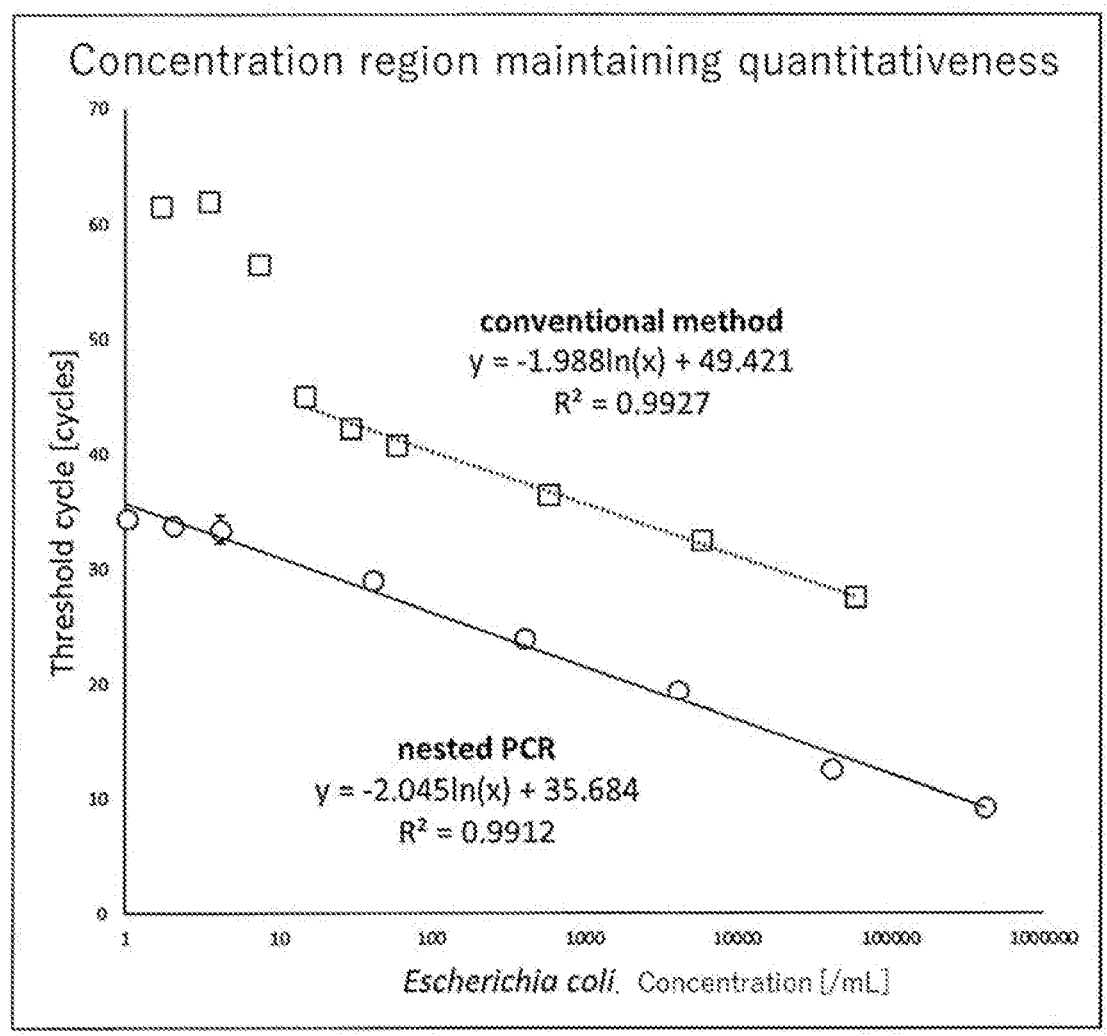
FIG. 3 The figure is a graph showing quantitativeness of a conventional real-time PCR method (conventional PCR method) in comparison with a nested PCR method according to the present invention.

FIG. 3 shows a graph showing quantitativeness by a conventional real-time PCR method (conventional PCR method) (displayed by □) in comparison with quantitativeness by a nested PCR method (displayed by ○) according to the present invention.

Specific conditions for the nested PCR will be described for reference.

The nested PCR was carried out by repeatedly subjecting a reaction solution having the following composition 1 to a reaction cycle consisting of heating at 95° C. for 5 minutes and reactions at 94° C. for 10 seconds, at 57° C. or 62° C. for 10 seconds, at 72° C. for 30 seconds and at 82° C. for 2 seconds, for 30 times ($1^{st}$ PCR).

<Reaction Solution Composition 1>
  Template 2 µL
  10× Buffer for rTaq or 10× Thunder Taq buffer 2 µL
  25 mM MgCl₂ 1.6 to 1.8 µL
  Yeast-produced Taq DNA polymerase 1 Unit
  2 mM CleanAmp-dNTP 2 µL
  EvaGreen 1 µL
  10 µM Region 1 forward primer 1a, 1b (equivalent amount), 0.8 to 1.2 µL in total
  10 µM Region 7 reverse primer 0.6 to 1.2 µL (In pattern 2, Region 7 reverse primer 1a and 1b (equivalent amount), 1.2 µL in total)
  Sterile water: appropriate amount
  Total 20 µL After completion of the PCR, the reaction solution was recovered and diluted 100 fold with DNA-free ultrapure water. The diluted solution was used as a template, a reaction was carried out with the reaction solution having composition 2 shown below ($2^{nd}$ PCR). The PCR reaction was carried out by repeating a cycle consisting of heating at 95° C. for 5 minutes, reactions at 94° C. for 10 seconds, at 57° C. for 10 seconds, at 72° C. for 10 seconds and at 82° C. for 10 seconds, for 35 times. Note that, the forward primer and reverse primer to be used in this step were pattern 1 for second PCR step, and forward primers and reverse primers for individual regions 1 to 7 were used as primer pairs.

<Reaction Solution Composition 2>
  Template 10 µL
  10× Thunder Taq buffer 2 µL
  25 mM MgCl₂ 2 µL
  Yeast-produced Taq DNA polymerase 1 Unit
  2 mM CleanAmp-dNTP or conventional dNTP 2 µL
  EvaGreen 1 µL
  10 µM forward primer 0.6 µL
  10 µM reverse primer 0.6 µL
  Sterile water: appropriate amount
  Total 20 µL Note that a conventional real-time PCR ($1^{st}$ PCR was not carried out and the same conditions as in the $2^{nd}$ PCR) was carried out by extending the number of repeats up to 60. In particular, the results obtained using the primer pair for region 3 and exhibiting high quantitativeness were shown in FIG. 3 as a comparison.

In the conventional real-time PCR, quantification in a low concentration region cannot be made; however, if a cycle of nested PCR is repeated such that gene amplification by $1^{st}$ PCR does not reach a plateau, a calibration curve maintaining linearity even in a low concentration region can be obtained, with the result that highly sensitive/accurate determination of the number/species of a pathogenic bacterium can be made. It was confirmed that a bacterial number (*E. coli.*) of 1 to up to 400,000 per PCR tube can be determined by the method of the invention.

With respect to relationship between *Escherichia coli* concentration (represented by □ in FIG. 3) and threshold of the number of PCR cycles, linearity in the relationship is not established in a low concentration region of 10 cells/ml or less. From the results, it is found that quantitativeness is not maintained in a low concentration region in a conventional PCR method.

Figure 4:
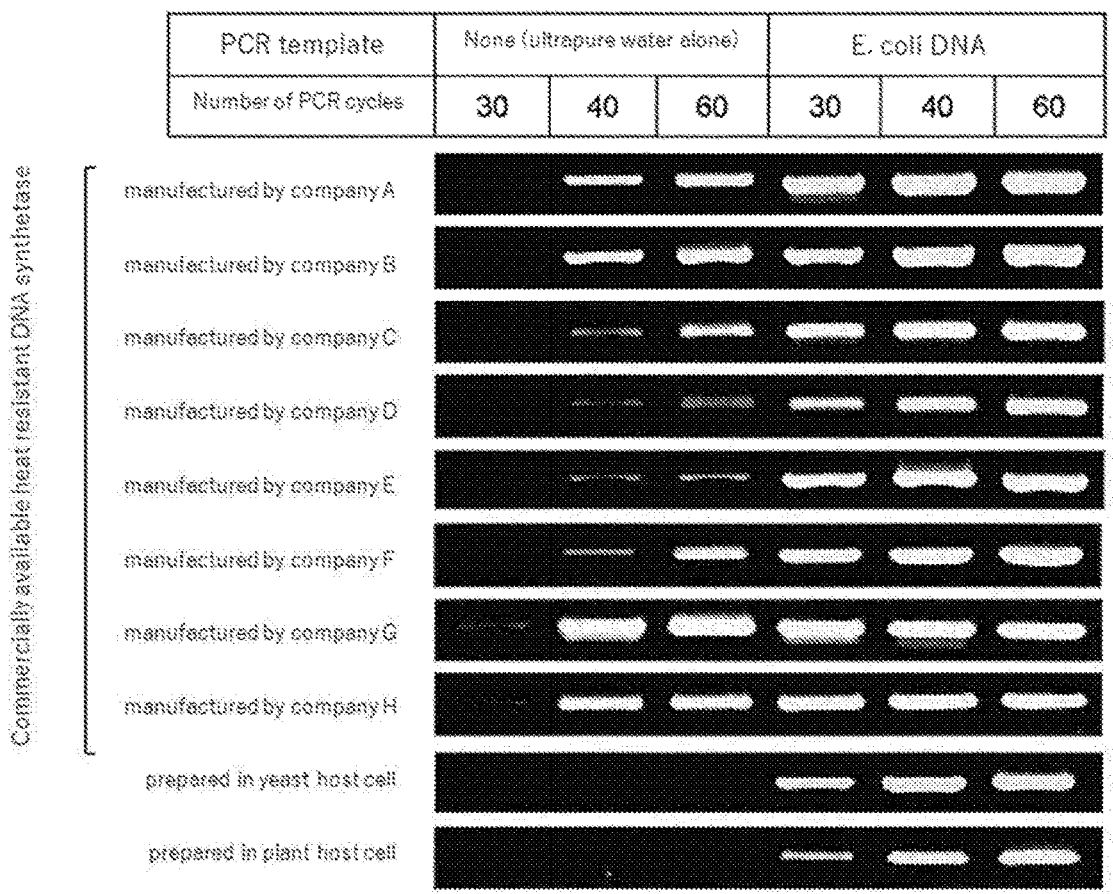
FIG. 4 The figure shows the detection results of DNA derived from a host bacterium and remaining in heat-resistant DNA polymerase (commercially available heat-resistant DNA polymerases and the heat-resistant DNA polymerase produced from a eukaryote as a host).

Using a heat resistant DNA polymerase, which was produced in a eukaryotic organism (eukaryote-made Taq DNA polymerase) according to Patent Literature 2, bacterial universal PCR is carried out without contamination with bacterial DNA. In this manner, the background due to bacterial contamination is reduced to zero and an extremely small number of pathogenic bacterial cells can be accurately determined (if no bacterium is present, the bacterial number may be zero). To confirm this, using a bacterial universal primer, PCR was carried out in the presence or absence of DNA of *Escherichia coli* serving as a template. Thereafter, the PCR amplification product was subjected to agarose gel electrophoresis. As a result, when commercially available heat-resistant DNA synthetase was used, residual bacterial DNA was found; whereas no bacterial DNA was found when eukaryote-made Taq DNA polymerase (prepared using a yeast or a plant cell as a host) was used (FIG. 4).

(Step 3: Rapid Identification of Pathogenic Bacterium by Tm Mapping Method (Carried Out Concurrently with Step 4))

Using DNA obtained in Step 1 as a template, a pathogenic bacterium was identified by a Tm mapping method in the PCR conditions of Step 2.

Figure 5:
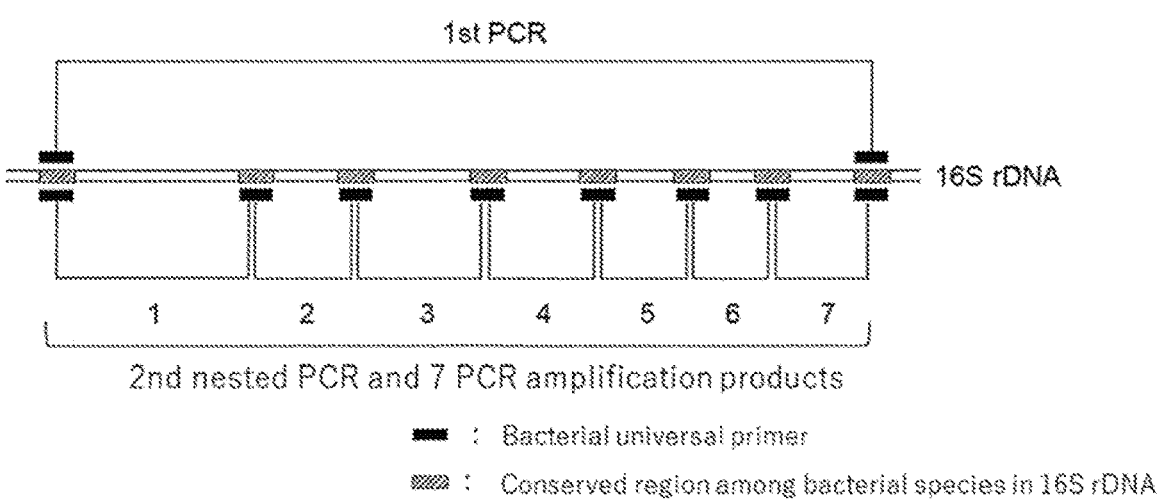
FIG. 5 The figure shows arrangement of primers for Tm mapping (method) in 16S rRNA.

In the Tm mapping method, the arrangement of individual primers are shown in FIG. 5 and the sequences of the primers used in this example are shown below.

The primer sequences used in this example
1st PCR:
The following Region 1' forward primers 1a and 1b are mixed in a quantitative ratio of 1:1 and put in use.

Similarly, Region 7' reverse primers 1a and 1b are mixed in a quantitative ratio of 1:1 and put in use.

1st PCR is carried out by placing a single specimen in a single tube.

```
Region 1' forward primer 1a:
                                (SEQ ID No. 1)
5'-AGAGTTTGATCATGGCTCAG-3'

Region 1' forward primer 1b:
                                (SEQ ID No. 2)
5'-AGAGTTTGATCCTGGCTCAG-3'

Region 7' reverse primer 1a:
                                (SEQ ID No. 4)
5'-AGACCCGGGAACGTATTC-3'

Region 7' reverse primer 1b:
                                (SEQ ID No. 5)
5'-AGGCCCGGGAACGTATTC-3'
```

2nd (nested) PCR:

PCR is carried out by placing the following Region 1' to 7' forward and reverse primer sets separately in a single tube (7 tubes in total per single specimen) to obtain seven Tm values, and then, a pathogenic bacterium was rapidly identified by the Tm mapping method.

```
Region 1' forward primer:
                                (SEQ ID No. 18)
5'-GCAGGCTTAACACATGCAAGTCG-3'

Region 1' reverse primer:
                                (SEQ ID No. 6)
5'-CGTAGGAGTCTGGACCGT-3'

Region 2' forward primer:
                                (SEQ ID No. 19)
5'-GTCCAGACTCCTACGGGAG-3'

Region 2' reverse primer:
                                (SEQ ID No. 20)
5'-CCTACGTATTACCGCGG-3'

Region 3' forward primer:
                                (SEQ ID No. 21)
5'-AGCAGCCGCGGTAATA-3'
```

```
Region 3' reverse primer:
                                   (SEQ ID No. 10)
5'-GGACTACCAGGGTATCTAATCCT-3'

Region 4' forward primer:
                                   (SEQ ID No. 11)
5'-AACAGGATTAGATACCCTGGTAG-3'

Region 4' reverse primer:
                                   (SEQ ID No. 12)
5'-AATTAAACCACATGCTCCACC-3'

Region 5' forward primer:
                                   (SEQ ID No. 13)
5'-TGGTTTAATTCGATGCAACGC-3'

Region 5' reverse primer:
                                   (SEQ ID No. 14)
5'-GAGCTGACGACAGCCAT-3'

Region 6' forward primer:
                                   (SEQ ID No. 22)
5'-GTTAAGTCCCGCAACGAG-3'

Region 6' reverse primer:
                                   (SEQ ID No. 23)
5'-CCATTGTAGCACGTGTGTAGCC-3'

Region 7' forward primer:
                                   (SEQ ID No. 24)
5'-GGCTACACACGTGCTACAATGG-3'

Region 7' reverse primer:
                                   (SEQ ID No. 4)
5'-AGACCCGGGAACGTATTC-3'
```

(Step 4: Method for Determining the Number of Pathogenic Bacterial Cells with No Difference Between Bacterial Species (Carried Out Concurrently with Step 3))

In order to prepare a calibration curve for quantification, DNA was extracted from a bacterium of a known cell number, serially diluted to prepare 3 DNA solutions different in concentration and used as quantification controls. A method for preparing the quantification controls is shown below.

(A) DNA was Extracted from a Bacterium of a Previously Known Bacterial Number to Prepare a DNA Extract (1) *Escherichia coli* ATCC25922 strain was scattered onto a normal agar medium, and then cultured in an incubator for 12 hours.

(2) a suspension (McFarland 0.5) was prepared with physiological saline.

(3) 1000-fold dilution was made and the number of bacterial cells was counted using BD cell viability kit and BD FACS Canto II.

(4) Measurement was repeated three times in total, and an average value thereof was used as the number of bacterial cells (140605 cells/ml).

(5) DNA was extracted from the diluted solution (100 µl, 14061 cells) and finally a DNA extract of AVE (100 µl) (DNA extract of DNA extraction kit manufactured by QIAGEN) was prepared (140 cells/µl).

(B) Preparation of a Large-Volume DNA Extract for a Quantification Control (1) *Escherichia coli* ATCC25922 strain was scattered on normal agar medium and then cultured in an incubator for 12 hours.

(2) a suspension (McFarland 0.5) was prepared with physiological saline.

(3) DNA was extracted from the suspension (1 ml) and finally a DNA extract of AVE (100 µl) was prepared.

(C) Correction of Number of Bacterial Cells in the Large-Volume DNA Extract of Section (B) Using a DNA Extract Prepared from a Bacterium of a Previously Known Number of Bacterial Cells (1) The DNA extract prepared in the step of Section (B) was diluted with AVE. The number of bacterial cells in the diluted DNA extract was determined with the calibration curve described in Section (A).

(2) Finally, a 5000 cells/µl DNA extract was prepared in a large amount.

(3) The DNA extract (15 µl) was divided into portions of 1.5-ml tubes and stored at −80° C.

(4) In use for quantification test, each of the DNA extract portions divided was diluted with AVE, 10 fold, 100 fold and 1000 fold and put in use. As a result, 500 cells/µl (1000 cells/PCR tube), 50 cells/µl (100 cells/PCR tube) and 5 cells/µl (10 cells/PCR tube) DNA extracts were prepared. A calibration curve was prepared using these 3 concentration DNA extracts.

Subsequently, using pathogenic bacterium DNA of Step 1 as a template, nested PCR was carried out together with a quantification control in the conditions described in Step 2. In the 1st PCR and 2nd PCR for quantification, the following bacterial universal primer (primer for detecting almost all bacteria) was used. The target region of the bacterial universal primer is a bacterial conserved region (base sequence region common in almost all bacteria) of a 16S ribosomal RNA gene. A predetermined bacterium is quantified by a bacterial species-specific primer; however, a pathogenic bacterium is not identified in the early stage of sepsis. Because of this, a bacterial species-specific primer cannot be used. Accordingly, unless a bacterial universal primer is used, an unidentified bacterium cannot be detected.

However, if a single base mismatch is present between a primer and a target region, a quantitative result is affected (measurement value is lower than an actual value). The base sequences of the bacterial conserved regions are not always completely identical in all bacteria. There are cases where two conserved sequences differ in single base. In this case, if a primer which perfectly matches to one of the conserved sequences is used, in a bacterium having a single base mismatch, the measurement value (quantitative results) is lower than an actual value. To overcome this problem in the present invention, primers completely matching respectively to the sequences which mutually differ in single base are mixed in equal amounts. In this manner, accurate quantification of both sequences was successfully attained. In the following, experimental results showing that accurate quantification of both sequences was able to be made by mixing an equal amount of two types of primers to be completely match to the sequences, are shown (FIG. 6).

Figure 6:
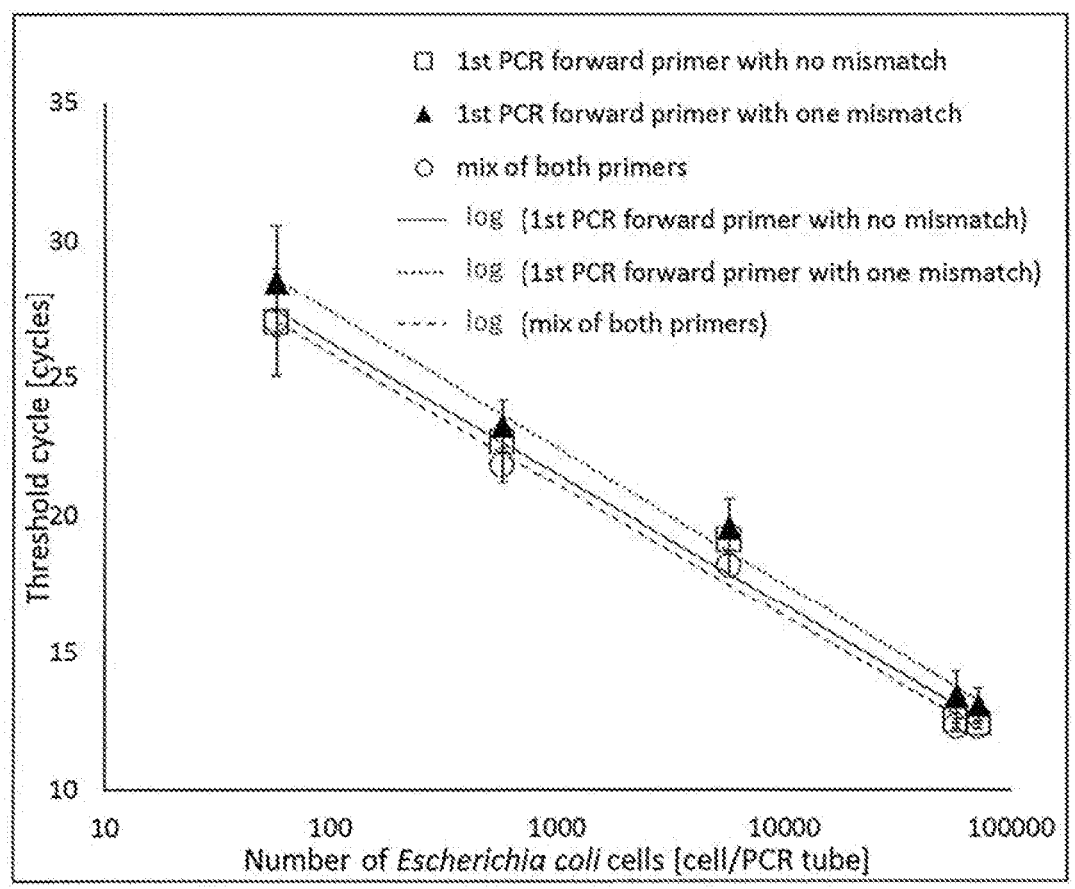
FIG. 6 The figure shows experimental results of enabling accurate quantification by mixing primers different in a single base in equivalent amounts.

Illustration of experiment shown in FIG. 6:

With respect to the bacterial conserved region of bacterial 16S ribosomal RNA gene, for example, if the pattern 1 primer set is used in the Tm mapping method, the target sequences of the 1st PCR forward primer in all bacterial species are divided into two types of sequences represented by primarily AGAGTTTGATCATGGCTCAG (SEQ ID No. 1) and AGAGTTTGATCCTGGCTCAG (SEQ ID No. 2), which differ in single base.

Then, we used the following 3 types of 1st PCR forward primers (a reverse primer was used in common) and the DNA sample of *Escherichia coli* (target sequence of the forward primer: AGAGTTTGATCATGGCTCAG: SEQ ID No. 1) as a template, and prepared dilution series to prepare a standard curve.

1st PCR forward primer with no mismatch against *E. coli*
(AGAGTTTGATCATGGCTCAG:SEQ ID No. 1)
1st PCR forward primer with one mismatch against *E. coli*
(AGAGTTTGATCCTGGCTCAG: SEQ ID No. 2)
a mix of both $1^{st}$ PCR forward primers (no mismatch: one mismatch=1:1)

As a result of PCR using $1^{st}$ PCR forward primer with one mismatch, the quantitative result decreased up to about 75%, compared to PCR using 1st PCR forward primer with no mismatch. However, if a mix of both 1st PCR forward primers (no mismatch: one mismatch=1:1) was used, the quantitative result was almost the same as those of the case where $1^{st}$ PCR forward primer with no mismatch was used.

In other words, if a mix of both 1st PCR forward primers (no mismatch: one mismatch=1:1) was used, even if either one of sequences AGAGTTTGATCATGGCTCAG (SEQ ID No. 1) and AGAGTTTGATCCTGGCTCAG (SEQ ID No. 2) was used, it was shown that accurate quantification can be equally made.

PCR primer sets for quantification used in this Example are shown below.

1st PCR;

The following Region 1' forward primers 1a and 1b are mixed in a quantitative ratio of 1:1 and put in use.

Similarly, Region 7' reverse primers 1a and 1b are mixed in a quantitative ratio of 1:1 and put in use.

```
Region 1' forward primer 1a:
                          (SEQ ID No. 1)
5'-AGAGTTTGATCATGGCTCAG-3'

Region 1' forward primer 1b:
                          (SEQ ID No. 2)
5'-AGAGTTTGATCCTGGCTCAG-3'

Region 7' reverse primer 1a:
                          (SEQ ID No. 4)
5'-AGACCCGGGAACGTATTC-3'

Region 7' reverse primer 1b:
                          (SEQ ID No. 5)
5'-AGGCCCGGGAACGTATTC-3'
```

2nd (nested) PCR;

The following Region 3' forward primer and Region 3' reverse primer are used.

```
Region 3' forward primer:
                          (SEQ ID No. 21)
5'-AGCAGCCGCGGTAATA-3'

Region 3' reverse primer:
                          (SEQ ID No. 10)
5'-GGACTACCAGGGTATCTAATCCT-3'
```

As mentioned above, *E. coli* DNA samples of three different concentrations and of a known bacterial number were used as quantification controls. Based on the data of three quantification controls different in concentration, a calibration curve was prepared. Based on bacterial DNA extracted from a patient specimen, the number of pathogenic bacterial cells was determined. Since the number of bacterial cells was obtained as an *E. coli* cell-number equivalent used as a quantification control, the number of bacterial cells in a specimen can be more easily, rapidly and accurately determined.

Step 1 to Step 4 mentioned above is one of Examples of the first quantification method according to the present invention.

(Step 5: Correction of Number of Bacterial Cells by 16S Ribosomal RNA Operon Copy Number Using the Results of Rapid Identification of Pathogenic Bacterium)

In the above, quantitative results as the number of *E. coli* cells (which were used as a quantification control in Step 4) were computationally obtained. The target gene used in quantification is 16S ribosomal RNA gene. As a great many 16S ribosomal RNA operon copy numbers in bacterial genomes are shown in Table 1, the operon copy number of a 16S ribosomal RNA gene varies depending on the bacterial species. Because of this, the number expressed as *E. coli* cell number does not always represent the cell number of other bacterial species.

TABLE 1

| Name of bacterial species | 16S rRNA operon copy number |
|---|---|
| *Bacillus cereus* | 13 |
| *Clostridium difficile* | 12 |
| *Aeromonas hydrophila* | 10 |
| *Clostridium perfringens* | 10 |
| *Enterobacter aerogenes* | 8 |
| *Enterobacter cloacae* | 8 |
| *Klebsiella pneumoniae* | 8 |
| *Bacteroides vulgatus* | 7 |
| *Escherichia coli* | 7 |
| *Streptococcus agalactiae* | 7 |
| *Bacteroides fragilis* | 6 |
| *Enterococcus faecium* | 6 |
| *Bacteroides distasonis* | 5 |
| *Staphylococcus aureus* | 5 |
| *Staphylococcus epidermidis* | 5 |
| *Staphylococcus haemolyticus* | 5 |
| *Staphylococcus lugdunensis* | 5 |
| *Streptococcus dysagalactiae* | 5 |
| *Enterococcus faecalis* | 4 |
| *Lactobacillus acidophilus* | 4 |
| *Lactobacillus crispatus* | 4 |
| *Peptostreptococcus magnus* | 4 |
| *Peptostreptococcus prevotii* | 4 |
| *Pseudomonas aeruginosa* | 4 |
| *Streptococcus mitis* | 4 |
| *Eubacterium lentum* | 3 |
| *Campylobacter jejuni* | 3 |
| *Propionibacterium acnes* | 3 |
| *Acinetobacter catcoaceticus* | 2 |
| *Gardnerella vaginalis* | 2 |
| *Ureaplasma parvum* | 2 |
| *Ureaplasma urealyticum* | 2 |
| *Mycoplasma horminis* | 2 |
| *Mycoplasma genitalium* | 1 |
| *Mycoplasma pneumoniae* | 1 |

For the reason, it is necessary to make a correction based on the operon copy number per bacterium species in order to more accurately determine bacterial number. Since identification and qualification of a pathogenic bacterium are carried out concurrently in Step 3 and Step 4, the number of pathogenic bacterial cells can be corrected based on 16S ribosomal RNA operon copy number of the bacterium identified to computationally obtain the correct number of bacterial cells.

To describe more specifically, a calibration curve is prepared using *Escherichia coli* as a control bacterium. If the bacterium identified in a specimen is *Bacillus cereus*, the number of the bacterial cells can be corrected according to the computational expression:

Corrected number of bacterial cells=provisional number of bacterial cells×(7/13).

Step 1 to Step 5 mentioned above is one of Examples of the second quantification method according to the present invention.

Example 2

According to Step 1 to Step 4 of Example 1, a pathogenic bacterium rapid quantification test using sepsis patient's specimens (EDTA blood collection tube, 2 mL) was carried out. Three cases of patients who were suspected of having sepsis at the Toyama University Hospital and thereafter showed a positive result in a blood culture test were used. Blood was sampled before treatment with an antibiotic (pretreatment), and 24 hours (after 24 hrs.) and 72 hours (after 72 hrs.) after administration of the antibiotic. At the three points, a pathogenic bacterium rapid quantification test was carried out together with measurement of body temperature, white blood cell count, CRP, presepsin and IL-6. Furthermore, a blood specimen sampled before the antibiotic treatment was subjected to a blood culture method to identify a pathogenic bacterium and subjected to a drug sensitivity test. General information about individual cases is as follows.

Case 1:
- 76 years old, woman, sepsis associated with urinary tract infection
- blood culture/urine culture: *Escherichia coli*
- antibiotic substance: meropenem (sensitive)

Case 2:
- 88 years old, woman, sepsis associated with obstructive cholangitis complicated with terminal-stage pancreatic cancer
- blood culture: *Klebsiella oxytoca, Haemophilus influenzae, Streptococcus pneumoniae*
- antibiotics substance: cefepim (sensitive to *K. oxytoca* and *H. influenzae*; and showed medium-level sensitivity to *S. pneumoniae*)

Case 3:
- 94 years old, woman, sepsis associated with urinary tract infection
- blood culture/urine culture: *Escherichia coli*
- antibiotics substance: tazobactam/piperacillin (sensitive)

Figure 7:
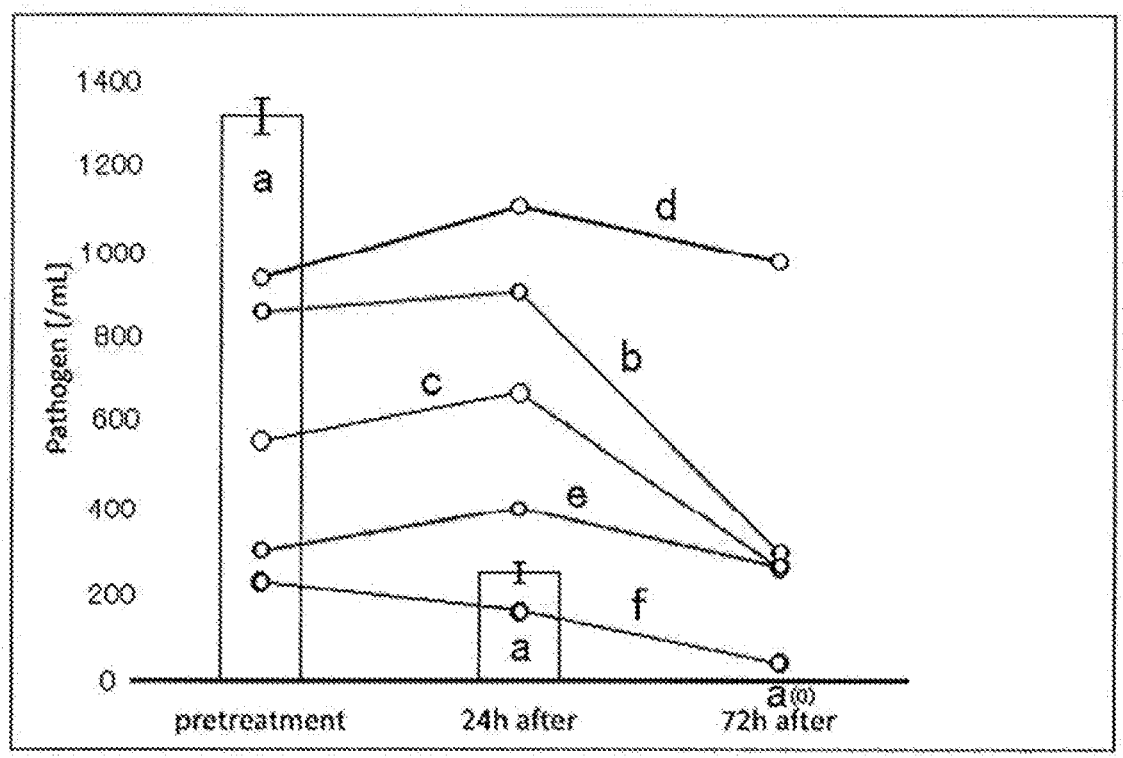
FIG. 7 The figure shows an example of quantitative results of pathogenic bacterium and comparison of dynamics of other biomarkers before and after antibiotic treatment.
Figure 8:
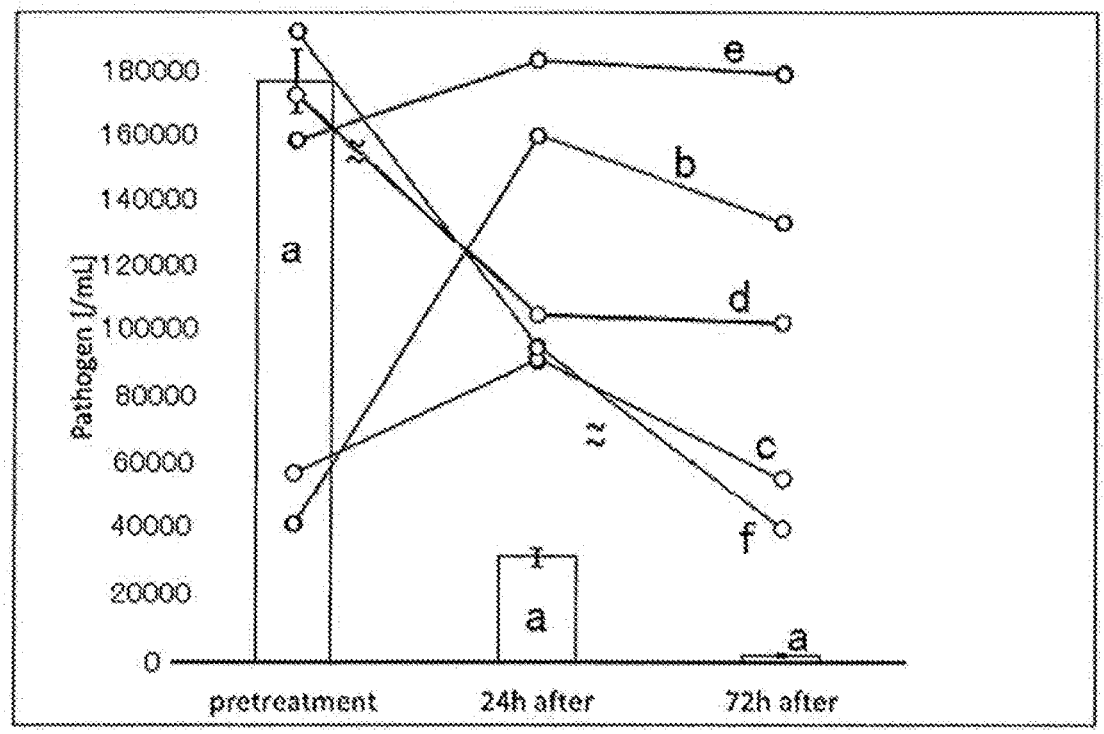
FIG. 8 The figure shows an example of quantitative results of pathogenic bacterium and comparison of dynamics of other biomarkers before and after antibiotic treatment.
Figure 9:
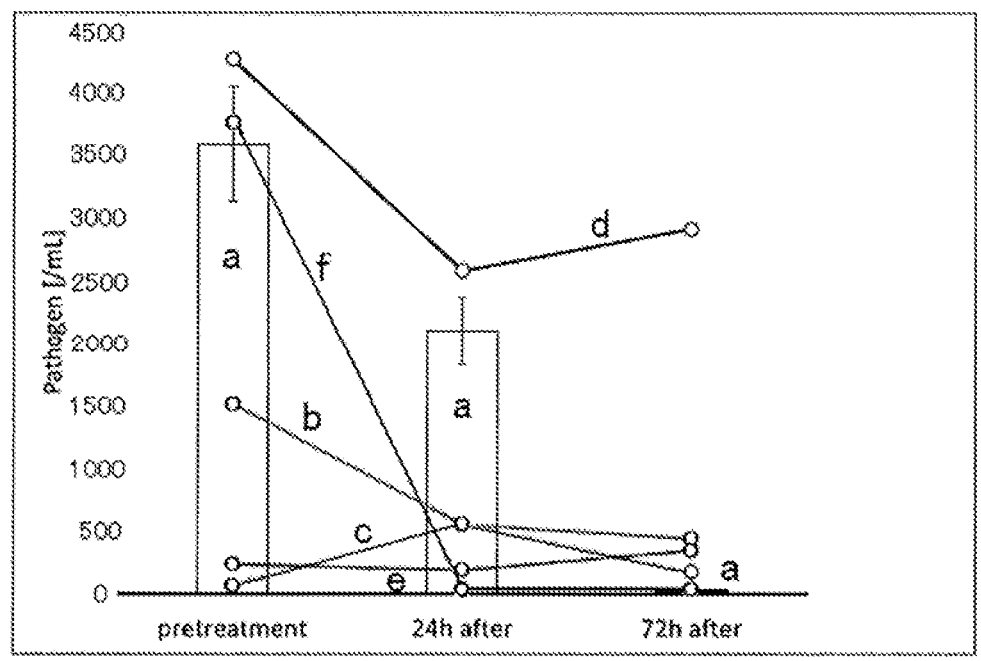
FIG. 9 The figure shows an example of quantitative results of pathogenic bacterium and comparison of dynamics of other biomarkers before and after antibiotic treatment.
Figure 10:
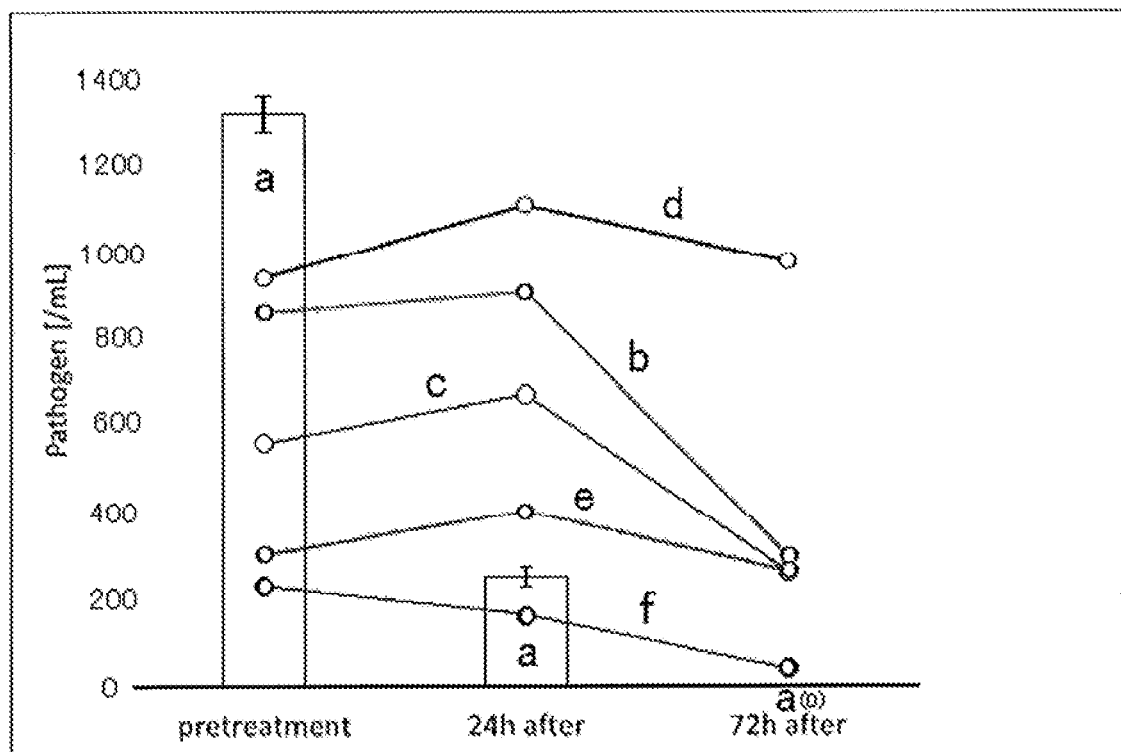
FIG. 10 The figure shows an example of quantitative results of pathogenic bacterium and comparison of dynamics of other biomarkers before and after antibiotic treatment.
Figure 11:
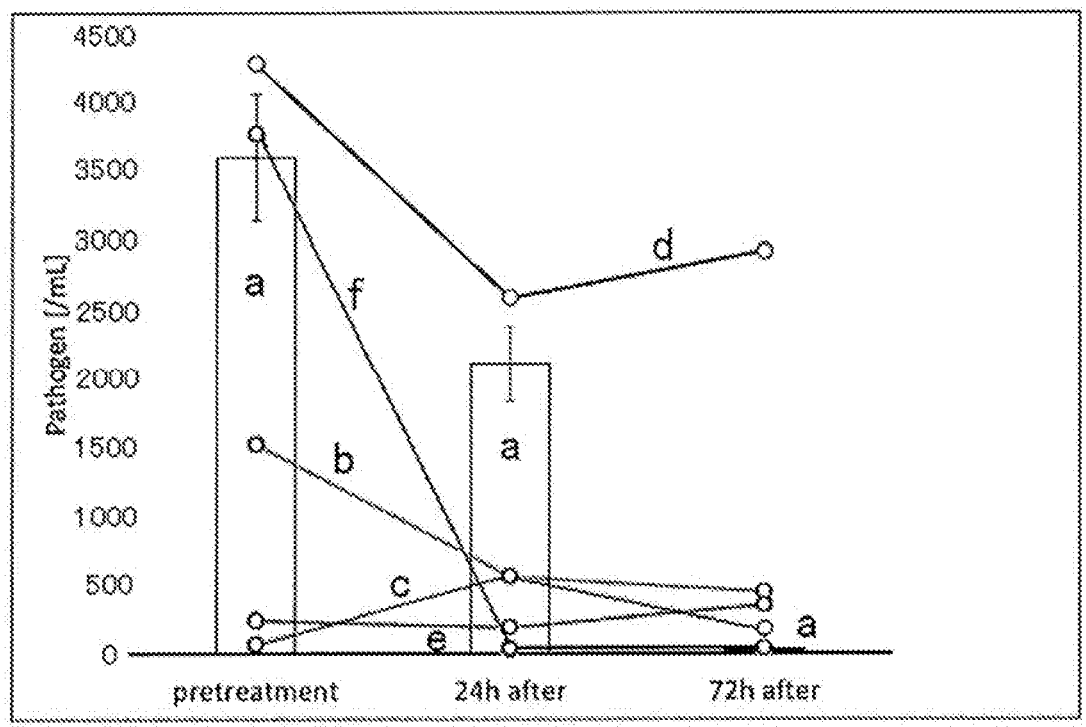
FIG. 11 The figure shows an example of quantitative results of pathogenic bacterium and comparison of dynamics of other biomarkers before and after antibiotic treatment.
Figure 12:
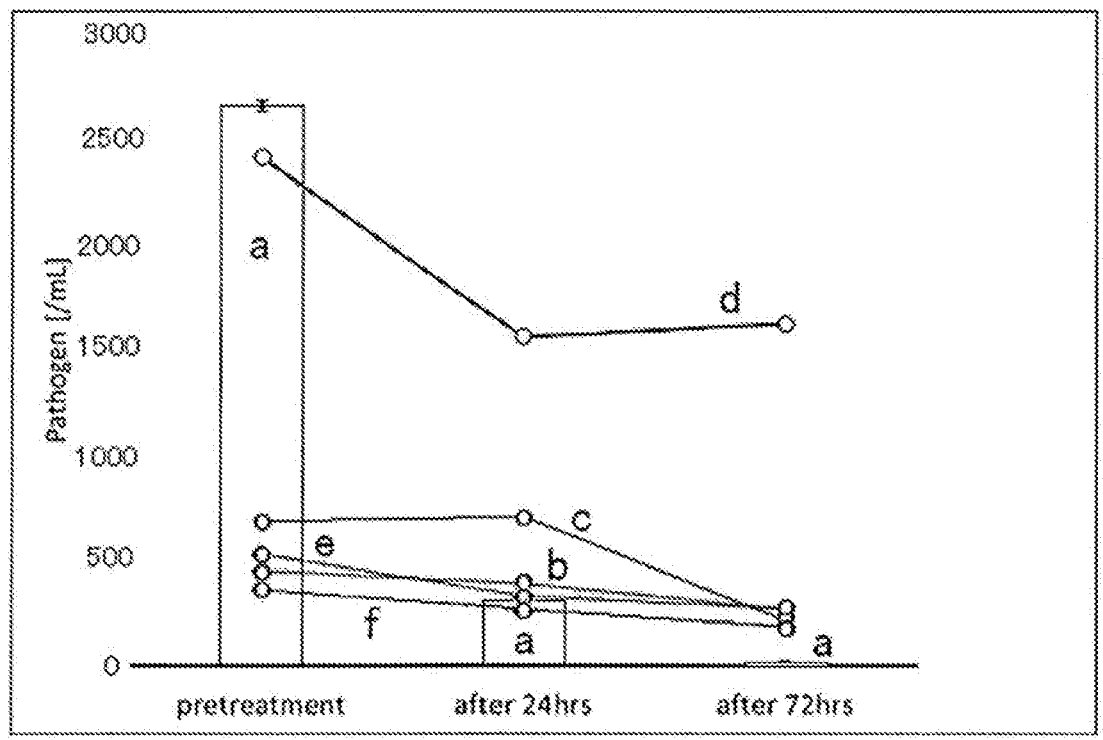
FIG. 12 The figure shows an example of quantitative results of pathogenic bacterium and comparison of dynamics of other biomarkers before and after antibiotic treatment.
Figure 13:
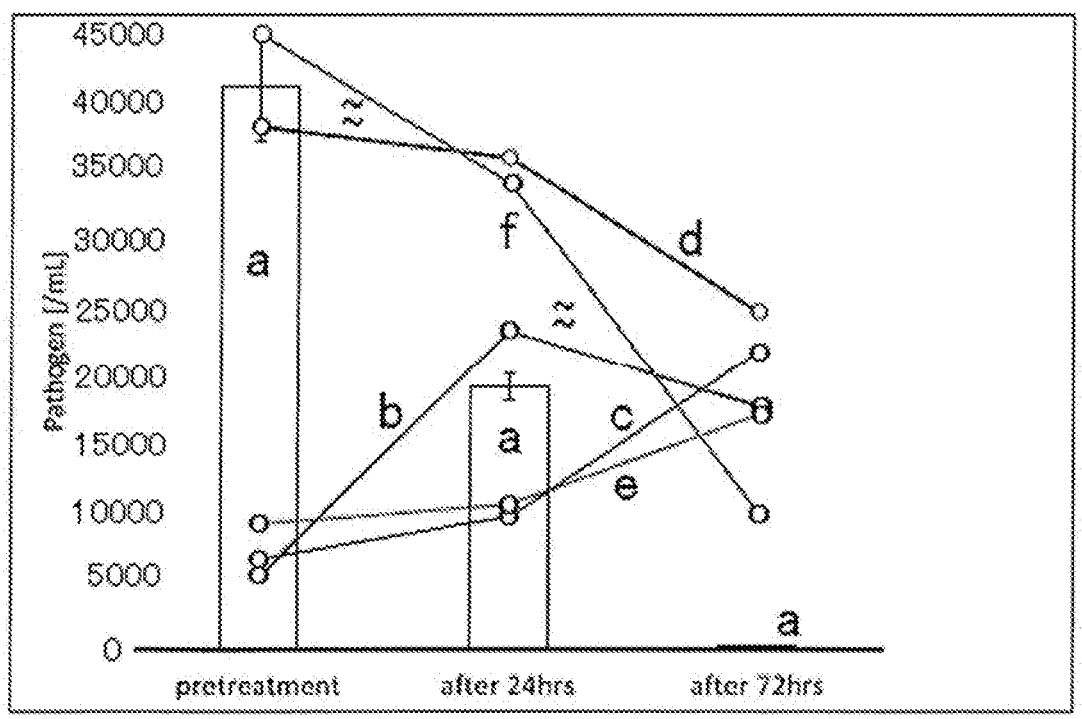
FIG. 13 The figure shows an example of quantitative results of pathogenic bacterial cells and comparison of dynamics of other biomarkers before and after antibiotic treatment.

The test results of individual cases are shown in Tables 2 to 4 and FIG. 7 to FIG. 9. Note that, reference symbols in FIGS. 7 to 9 represent the following measurement items. The measurement values at the positions indicated by "○" in individual figures are shown in the following tables.

- a: Pathogenic bacterium: pathogenic bacterium count measured by the method according to the present invention
- b: WBC: white blood cell count [×100/μL]
- c: CRP: C-reactive protein [mg/L]
- d: BT: body temperature (body temp.)[° C.]
- e: Presepsin [ng/mL]
- f: IL-6: interleukin-6 [pg/mL]

TABLE 2

(Case 1)

| Test item | | pretreatment | 24 h after | 72 h after |
|---|---|---|---|---|
| Pathogen | (cells/ml) (Ave) | 1314 | 248 | 0 |
| | SD | 43.578 | 23.271 | 0 |
| WBC | (×100/μL) | 285.6 | 301.4 | 98.7 |
| CRP | (mg/L) | 185.9 | 223.1 | 86.4 |
| BT | (° C.) | 37.0 | 37.9 | 37.2 |
| Presepsin | (ng/mL) | 1298 | 1729 | 1138 |
| IL-6 | (pg/mL) | 122 | 85.8 | 20.7 |

TABLE 3

(Case 2)

| Test item | | pretreatment | 24 h after | 72 h after |
|---|---|---|---|---|
| Pathogen | (cells/ml) (Ave) | 175270 | 31453 | 2066 |
| | SD | 9359 | 2522 | 226 |
| WBC | (×100/μL | 108.8 | 418.1 | 348.7 |
| CRP | (mg/L) | 150.3 | 240.0 | 145.5 |
| BT | (° C.) | 39.2 | 36.4 | 36.3 |
| Presepsin | (ng/mL) | 5379 | 6202 | 6060 |
| IL-6 | (pg/mL) | 122000 | 7400 | 168 |

TABLE 4

(Case 3)

| Test item | | pretreatment | 24 h after | 72 h after |
|---|---|---|---|---|
| Pathogen | (cells/ml) (Ave) | 3600 | 2102 | 2 |
| | SD | 451.2 | 277.9 | 0.1 |
| WBC | (×100/μL) | 168.3 | 61.4 | 49.2 |
| CRP | (mg/L) | 1.1 | 9.3 | 2.9 |
| BT | (° C.) | 39.6 | 36.6 | 37.2 |
| Presepsin | (ng/mL) | 343 | 267 | 501 |
| IL-6 | (pg/mL) | 678 | 5 | 6.3 |

Example 3

According to Step 1 to Step 5 of Example 1, a pathogenic bacterium rapid identification/quantification test using sepsis patient's specimens (EDTA blood collection tube, 2 mL) was carried out. Four cases of patients who were suspected of having sepsis at the Toyama University Hospital and thereafter showed a positive result in a blood culture test were used. Blood was sampled before treatment with an antibiotic (pretreatment), and 24 hours (after 24 hrs.) and 72 hours (after 72 hrs.) after administration of the antibiotic. At the three points, a pathogenic bacterium rapid identification/quantification test was carried out together with measurement of body temperature, white blood cell count, CRP, presepsin and IL-6. Furthermore, a blood specimen sampled before the antibiotic treatment was subjected to a blood culture method to identify a pathogenic bacterium and subjected to a drug sensitivity test. General information about individual cases is as follows.

Case 4:
- 76 years old, woman, sepsis associated with urinary tract infection
- Tm mapping method: *Escherichia coli* (Dist. value=0.29)
- blood culture/urine culture: *Escherichia coli*
- antibiotics substance: meropenem (sensitive)

Case 5:
- 94 years old, woman, sepsis associated with urinary tract infection
- Tm mapping method: *Escherichia coli* (Dist. value=0.19)
- blood culture/urine culture: *Escherichia coli*
- antibiotics substance: tazobactam/piperacillin (sensitive)

Case 6:
- 84 years old, woman, sepsis associated with wound infection after anterior lumbar fixation operation
- Tm mapping method: *Streptococcus dysgalactiae* (Dist. value=0.28)
- blood culture: *Streptococcus dysgalactiae*
- antibiotics substance: tazobactam/piperacillin (no criteria for evaluation of sensitivity)

Case 7:
- 81 years old, woman, sepsis associated with urinary tract infection
- Tm mapping method: *Enterobacter aerogenes* (Dist. value=0.48)
- blood culture/urine culture: *Enterobacter aerogenes* (two types of mutant strains)
- antibiotics substance: tazobactam/piperacillin (sensitive)

The test results of individual cases are shown in Tables 5 to 8 and FIG. 10 to FIG. 13. Note that, reference symbols in FIGS. 7 to 10 represent the following measurement items. The measurement values at the positions indicated by "○" in individual figures are shown in the following tables.

- a: Pathogenic bacterium: pathogenic bacterium count measured by the method according to the present invention
- b: WBC: white blood cell count [×100/μL]
- c: CRP: C-reactive protein [mg/L]
- d: BT: body temperature (body temp.)[° C.]
- e: Presepsin [ng/mL]
- f: IL-6: interleukin-6 [pg/mL]

TABLE 5

(Case 4)

| Test item | | pretreatment | 24 h after | 72 h after |
|---|---|---|---|---|
| Pathogen | (cells/ml) (Ave) | 1314 | 248 | 0 |
| | SD | 43.578 | 23.271 | 0 |
| WBC | (×100/μL) | 285.6 | 301.4 | 98.7 |
| CRP | (mg/L) | 185.9 | 223.1 | 86.4 |
| BT | (° C.) | 37.0 | 37.9 | 37.2 |
| Presepsin | (ng/mL) | 1298 | 1729 | 1138 |
| IL-6 | (pg/mL) | 122 | 85.8 | 20.7 |

TABLE 6

(Case 5)

| Test item | | pretreatment | 24 h after | 72 h after |
|---|---|---|---|---|
| Pathogen | (cells/ml) (Ave) | 3600 | 2102 | 2 |
| | SD | 451.2 | 277.9 | 0.1 |
| WBC | (×100/μL) | 168.3 | 61.4 | 49.2 |
| CRP | (mg/L) | 1.1 | 9.3 | 2.9 |
| BT | (° C.) | 39.6 | 36.6 | 37.2 |
| Presepsin | (ng/mL) | 343 | 267 | 501 |
| IL-6 | (pg/mL) | 678 | 5 | 6.3 |

TABLE 7

(Case 6)

| Test item | | pretreatment | 24 h after | 72 h after |
|---|---|---|---|---|
| Pathogen | (cells/ml)(Ave) | 2651 | 308 | 20 |
| | SD | 31.37 | 3.011 | 2.312 |
| WBC | (×100/μL) | 89.5 | 77.3 | 54.1 |
| CRP | (mg/L) | 136.1 | 139.8 | 43.2 |
| BT | (° C.) | 39.7 | 37.0 | 37.2 |
| Presepsin | (ng/mL) | 1373 | 854 | 708 |
| IL-6 | (pg/mL) | 115 | 85.3 | 59.4 |

TABLE 8

(Case 7)

| Test item | | pretreatment | 24 h after | 72 h after |
|---|---|---|---|---|
| Pathogen | (cells/ml) (Ave) | 41083 | 19156 | 59 |
| | SD | 3903 | 1049 | 1.952 |
| WBC | (×100/μL) | 59.4 | 258.5 | 198.2 |
| CRP | (mg/L) | 72.3 | 107 | 241.4 |
| BT | (° C.) | 38.8 | 38.4 | 36.4 |
| Presepsin | (ng/mL) | 1322 | 1516 | 2473 |
| IL-6 | (pg/mL) | 238000 | 41700 | 176 |

Example 4

According to Step 1 to Step 4 of Example 1, a pathogenic bacterium rapid identification/quantification test using a blood specimen of patients suspected of having sepsis (two EDTA blood collection tubes, 2 mL) was carried out. Note that the whole blood contained in one of the two blood collection tubes was centrifuged at 100×g for 5 minutes to separate blood cells. The resultant supernatant including buffy coat was recovered and uniformly stirred by a vortex mixer. From the resultant mixture, an aliquot of 500 μL was taken and centrifuged at a rate of 20,000×g for 10 minutes to obtain a pellet. In this procedure, bacterial cells were collected. The other tube was subjected to separation of blood cells as mentioned above. The resultant supernatant (500 μL) was recovered so as not to contain buffy coat, centrifuged at a high rate of 20,000×g for 10 minutes to obtain a pellet. In this procedure, bacterial cells were collected.

The sample containing buffy coat contains white blood cells which ingested bacterial cells by phagocytosis; whereas the sample containing no buffy coat is the plasma containing no white blood cells which ingested bacterial cells by phagocytosis. In the case that a patient and patient's specimen are not actually infected and that bacterial DNA derived from the skin-resident bacteria at the time of blood sampling, work environment and contamination of instruments was detected, it is meant that these bacterial cells were not ingested by white blood cells by phagocytosis, with the result that no difference is found in bacterial number in the samples regardless of the presence or absence of buffy coat. In contrast, if the bacterium detected herein is a pathogenic bacterium, the pathogenic bacterium should have ingested by white blood cells by phagocytosis in the patient's blood, with the result that number of bacterial cells of the sample containing buffy coat should be markedly larger than that in the sample containing no buffy coat.

The results obtained from individual specimens are shown in Tables 9 to 13.

TABLE 9

| | Bacterial number/ml, with buffy coat | Bacterial number/ml, without buffy coat | Presepsin | WBC | CRP | qSOFA | Body temperature | Culture |
|---|---|---|---|---|---|---|---|---|
| Specimen No. 41 | | | | | | | | |
| Disease Name | Urinary tract infection | Culture results: E. coli | | Tm: E.coli | | | No biotics at blood sampling | |
| Day 0 | 41,800 | 50 | 1,420 | 16,260 | 4.75 | 3 | 38.9 | E.coli |
| Day 1 | 850 | 0 | 1,103 | 14,320 | 16.5 | 2 | 37.2 | (not carried out) |
| Day 3* | 700 (unidentified) | 0 | 2,838 | 7,440 | 24.63 | 2 | 37.5 | (not carried out) |

*Complicated with ventilator-associated pneumonia

| Specimen No. 25 | | | | | | | | |
|---|---|---|---|---|---|---|---|---|
| Disease Name | Liver abscess | Culture results: K. pneumoniae, P. vulgaris | | Tm: K. pneumoniae | | | No biotics at blood sampling | |
| Day 0 | 125,781 | 4,400 | 3,181 | 14,620 | 17.66 | 3 | 38.1 | K. pneumoniae, P. vulgaris |
| Day 1 | 14,438 | less than 50 | 2,224 | 32,570 | 28.14 | 2 | 38.2 | (not carried out) |
| Day 3 | 394 | less than 50 | 778 | 14,720 | 11.92 | 1 | 39.1 | (not carried out |

| Specimen No. 28 | | | | | | | | |
|---|---|---|---|---|---|---|---|---|
| Disease Name | inflammation of vertebral body. Exradural abscess | Culture results: MSSA | | Tm: S. aureus | | | No biotics at blood sampling | |
| Day 0 | 24,150 | 4,410 | 633 | 10,560 | 21.98 | 1 | 35.9 | MSSA |
| Day 1 | 4,340 | 350 | 695 | 20,040 | 22.34 | 1 | 36.5 | (not carried out) |
| Day 3 | 500 | 50 | 583 | 19,390 | 19.53 | 1 | 35.7 | (not carried out) |

TABLE 10

| | Bacterial number/ml, with buffy coat | Bacterial number/ml, without buffy coat | Presepsin | WBC | CRP | qSOFA | Body temperature | Culture |
|---|---|---|---|---|---|---|---|---|
| Specimen No. 31 | | | | | | | | |
| Disease Name | Urinary tract infection | Culture results: K. pneumoniae | | Tm: K. pneumoniae | | | No biotics at blood sampling | |
| Day 0 | 6,038 | 481 | 1,250 | 12,870 | 18.34 | 1 | 37.9 | K. pneumoniae |
| Specimen No. 39 | | | | | | | | |
| Disease Name | Peritoneum inflammation or CV infection | Culture results: S. capitis | | Tm: S. capitis | | | No biotics at blood sampling | |
| Day 0 | 42,642 | 292 | 2,789 | 30,890 | 33.56 | 1 | 37.8 | S. capitis |
| Specimen No. 43 | | | | | | | | |
| Disease Name | Urinary tract infection | Culture results: E. coli | | Tm: E.coli | | | No biotics at blood sampling | |
| Day 0 | 700 | 50 | 1,204 | 2,200 | 9.97 | 0 | 37.9 | E. coli |
| Day 1 | 250 | Negative | 1,659 | 14,380 | 19.04 | 0 | 36.3 | (not carried out) |
| Day 3 | 100 | Negative | 576 | 7,750 | 8.18 | 0 | 37.7 | (not carried out) |

TABLE 11

| | Bacterial number/ml, with buffy coat | Bacterial number/ml, without buffy coat | Presepsin | WBC | CRP | qSOFA | Body temperature | Culture |
|---|---|---|---|---|---|---|---|---|
| Specimen No. 78 | | | | | | | | |
| Disease Name | Esophageal fistula | Culture results: S. salvallus, S. oralis S. anginosus | | Tm: Plural types of bacteria (S. salvallus) | | | No biotics at blood sampling | |
| Day 0 | 58,900 | 50 | 559 | 5,620 | 1.09 | 2 | 37.7 | Plural types of bacteria |

TABLE 11-continued

| | Bacterial number/ml, with buffy coat | Bacterial number/ml, without buffy coat | Presepsin | WBC | CRP | qSOFA | Body temperature | Culture |
|---|---|---|---|---|---|---|---|---|
| Day 1 | 63,900 | 650 | 605 | 14,750 | 20.68 | 2 | 38.2 | (not carried out) |
| Day 3 | 5,200 | 200 | 1,094 | 7,260 | 12.35 | 2 | 38.7 | (not carried out) |

*Candidemia complication

Specimen No. 76

| | | | | | | | | |
|---|---|---|---|---|---|---|---|---|
| Disease Name | Catheter infection | Culture results: MRSE | | Tm: *S. epidermidis* (MecA-positive) | | | | |
| Day 0 | 56,490 | 280 | 715 | 12,220 | 0.47 | 0 | 39.7 | MRSE |
| Day 1 | 1050 (plural types of bacteria) | less than 50 | 267 | 9,980 | 6.15 | 0 | 37.1 | (not carried out) |
| Day 3 | 250 (plural types of bacteria) | less than 50 | 452 | 6,190 | 1.88 | 0 | 36.7 | (not carried out) |

Specimen No. 91

| | | | | | | | | |
|---|---|---|---|---|---|---|---|---|
| Disease Name | Skin infection | Culture results: MSSA | | Tm: *S. aureus* (MecA-No biotics at blood sampling) | | | | |
| Day 0 | 105,910 | less than 50 | 5,391 | 25080 | 19.29 | 3 | 37.8 | MSSA |
| Day 1 | 34,300 | less than 50 | 3,640 | 31370 | 22.71 | 1 | 37.8 | (not carried out) |
| Day 3 | 1,890 | less than 50 | 5,545 | 39880 | 31.48 | 1 | 37 | (not carried out) |

TABLE 12

| | Bacterial number/ml, with buffy coat | Bacterial number/ml, without buffy coat | Presepsin | WBC | CRP | qSOFA | Body temperature | Culture |
|---|---|---|---|---|---|---|---|---|

Specimen No. 105

| | | | | | | | | |
|---|---|---|---|---|---|---|---|---|
| Disease Name | Gallbladder inflammation | Culture results: *E. coli* | | Tm: *E. coli* | | | No biotics at blood sampling | |
| Day 0 | 4,650 | 50 | 862 | 11470 | 6.83 | 2 | 38.8 | *E. coli* |
| Day 1 | less than 50 (unidentified) | less than 50 | 521 | 8610 | 12.91 | 0 | 39 | (not carried out) |
| Day 3 | less than 50 (unidentified) | less than 50 | 920 | 5440 | 8.04 | 0 | 38.5 | (not carried out) |

Specimen No. 112

| | | | | | | | | |
|---|---|---|---|---|---|---|---|---|
| Disease Name | Ileus | Culture results: *Pseudomonas* sp | | Tm: *P. putida* | | | TAZ/PIPC at blood sampling | |
| Day 0 | 3,300 | less than 50 | 533 | 35410 | 6.5 | 3 | 40.3 | *Pseudomonas* sp |
| Day 1 | 1,000 | less than 50 | 634 | 88570 | 21.31 | 1 | 36.8 | (not carried out) |
| Day 3 | less than 50 (unidentified) | less than 50 | 324 | 8920 | 9.03 | 1 | 37.4 | Negative |

Specimen No. 120

| | | | | | | | | |
|---|---|---|---|---|---|---|---|---|
| Disease Name | Bile duct inflammation | Culture results: MSSA | | Tm: MSSA | | | No biotics at blood sampling | |
| Day 0 | 1,692 | less than 50 | 1,267 | 9460 | 9.99 | 1 | 36.5 | MSSA |

Specimen No. 124

| | | | | | | | | |
|---|---|---|---|---|---|---|---|---|
| Disease Name | Suppurative vertebral body intlammation/discitis | Culture results: MSSA | | Tm: MSSA | | | No biotics at blood sampling | |
| Day 0 | 2,625 | less than 50 | 456 | 12470 | 11.79 | 0 | 39.7 | MSSA |
| Day 1 | 467 | less than 50 | 426 | 11250 | 11.64 | 0 | 39.6 | (not carried out) |
| Day 3 | 583 | less than 50 | 633 | 7810 | 8.23 | 0 | 37.8 | (not carried out) |

TABLE 13

| Specimen No. | Disease | Bacterial species by Tm Mapping | Bacterial number/ml, with buffy coat | Bacterial number/ml, without buffy coat | Culture |
|---|---|---|---|---|---|
| 16 | Cellulitis/vertebral body inflammation | S. aureus (MRSA) | 210 | Negative | S. aureus |
| 54 | Enteritis | S. hominis | 200 | Negative | Negative |
| 66 | Bile duct inflammation | E. coli | 350 | less than 50 | E. coli |
| 66 | Urinary tract infection | K. pneumoniae | 250 | less than 50 | K. pneumoniae |
| 78 | Pneumonia | S. salivarius | 175 | Negative | Negative |
| 84 | Urinary tract infection | A. baumanii | 292 | 292 | Negative |
| 89 | Subcutaneous abscess | S. maltophilia | 87.5 | Negative | Negative |
| 98 | Gallbladder inflammation | S. pettenkoferi | 350 | less than 50 | Negative |
| 133 | Bile duct inflammation | K. pneumoniae | 262 | less than 50 | K. pneumoniae |
| 137 | unknown | S. lugdunensis | 450 | less than 50 | Negative |

In the results of specimens shown in Tables 9 and 10, the bacterial numbers of the specimens with buffy coat were larger and greatly exceed the number of bacterial cells of the specimens without buffy coat. From the results, it is possible to determine that bacterium identified by the Tm Mapping is a pathogenic bacterium with extremely high provability. Also with respect to these specimens, the same type of bacterium or bacterial species were markedly found in blood culture carried out concurrently with bacterial identification/quantification according to the method of the invention.

Table 11 shows that the specimens with buffy coat are large in bacterial number. From this, it was expected that the specimens were infected. However, compared with specimens in Table 9 and Table 10, the difference in bacterial number was low between specimens with or without buffy coat. In this case, it was presumed that a test with buffy coat might be accidentally contaminated or quantitative error might occur.

Then, sterile water was used as a sample, placed in a blood collection tube and subjected to the process from Step 1 to Step 4 of Example 1. The number of bacterial cells in the sample, which corresponds to a negative control, was determined multiple times. As a result, under this test environment, it was found that 100 cells/ml as the *Escherichia coli* number, is the numerical value, which is not derived from the original specimen but often detected.

In other words, even if a pathogenic bacterium is not present in a patient's specimen, a constant value of 100 cells/ml can be obtained despite the presence or absence of buffy coat, as an error. Even if the bacterial number differs between the samples with and without buffy coat, if the difference is 100 cells/ml or less, the difference can be a detection error.

In consideration of the result, the results shown in Table 11 can be interpreted as follows.

The bacterial numbers of Specimens No. 84 with and without buffy coat both exceeding 100 cells/ml fall within the error range but there is no difference in bacterial number. From this, it is determined that no phagocytosis by white blood cells occurred and the bacterium detected is not a pathogenic bacterium.

The bacterial number of Specimen No. 89 with buffy coat is 87.5 cells/ml, which is larger than the specimen without buffy coat but falls within the error range. From this, it cannot be determined that the bacterium detected is a pathogenic bacterium based on the bacterial number. The case is unable to determine.

In Specimen Nos. 16, 54, 56, 66, 78, 98, 133 and 137 with buffy coat, bacterial numbers exceed the error range and the difference in bacterial number from specimens without buffy coat exceeds the error range. There is a high possibility that the bacterium detected is a pathogenic bacterium.

Such a determination can be made in 4.5 hours, which is faster than the determination time of a few days in a conventional bacterial identification method by culturing.

As described in the foregoing, the number of bacterial cells in the blood dramatically changed beyond any other biomarkers in blood in a short period after treatment. From the results, it was suggested that the number of bacterial cells is a novel and excellent biomarker for sepsis. The test method of the invention, which can provide clinical data of bacterial numbers, for the first time in the world, is presumed to be extremely useful for future infectious disease medical care.

The invention claimed is:

1. A method for determining the number of test bacterial cells in a test specimen, comprising:
   (1) a first PCR step of carrying out a universal PCR method using a test nucleic acid derived from the test bacterial cells in the test specimen as a template and a universal primer pair for amplifying a bacterial 16S rRNA gene to obtain a universal test amplification product, wherein the universal test amplification product has a sequence comprising an internal sequence, wherein the universal primer pair comprises two forward primers in first equivalent amounts and two reverse primers in second equivalent amounts, wherein the two forward primers differ from each other in a first single base and/or the two reverse primers differ from each other in a second single base;
   (2) a second PCR step of carrying out a nested PCR method using a nested primer pair for amplifying the internal sequence to obtain a nested test amplification product; and
   (3) a bacterial cell number determination step of obtaining the number of the test bacterial cells in the test specimen based on the amount of the nested test amplification product and using calibration data showing a relationship between an amount of at least one nested control amplification product derived from at least one control sample of control bacterial cells of a known species and a cell number of the control bacterial cells in at least one control sample.

2. The method according to claim 1, further comprising the following steps before step (3):
   (4) a third PCR step of carrying out a universal PCR method using at least one control nucleic acid derived from the at least one control sample to obtain at least one universal control amplification product;
   (5) a fourth PCR step of carrying out a nested PCR method using the at least one universal control amplification product to obtain the at least one nested control amplification product; and
   (6) a step of preparing the calibration data based on the cell number of the control bacterial cells in the at least one control sample and the amount of the at least one nested control amplification product.

3. The method according to claim 2, wherein the at least one control sample comprises a plurality of control samples each having a different cell number of control bacterial cells, the at least one universal control amplification product comprises a plurality of universal control amplification products, and the at least one nested control amplification product comprises a plurality of nested control amplification products,
   wherein step (4) comprises independently using each of a plurality of nucleic acids derived from the plurality of control samples to obtain each of the plurality of universal control amplification products;
   wherein step (5) comprises using the plurality of universal control amplification products to obtain the plurality of nested control amplification products;
   wherein step (6) comprises preparing a calibration curve based on the cell number of the control bacterial cells in each of the plurality of control samples and the amount of each of the plurality of nested control amplification products; and
   wherein step (3) comprises using the calibration curve.

4. The method according to claim 1, wherein step (1) comprises controlling the number of cycles such that gene amplification does not reach a plateau.

5. The method according to claim 1, further comprising diluting a reaction solution to obtain a dilution solution, wherein the reaction solution comprises the universal test amplification product and subjecting the dilution solution to step (2).

6. The method according to claim 2, wherein step (1) and step (3) are carried out concurrently in a first PCR apparatus, and step (2) and step (4) are carried out concurrently in a second PCR apparatus.

7. The method according to claim 1, wherein step (2) comprises using a plurality of nested primer pairs each independently to obtain a plurality of nested test amplification products, the method further comprising identifying the species of the test bacterial cells in the test specimen based on a combination of the melting temperature (Tm) values of the plurality of nested test amplification products or a combination of differences in the Tm values.

8. The method according to claim 2, wherein step (2) comprises using a plurality of nested primer pairs each independently to obtain a plurality of nested test amplification products, the method further comprising identifying the species of the test bacterial cells in the test specimen based on a combination of the melting temperature (Tm) values of the plurality of nested test amplification products or a combination of differences in the Tm values, and wherein step (5) comprises using at least one of the plurality of nested primer pairs or the plurality of nested primer pairs each independently.

9. The method according to claim 1, wherein the known species of the control bacterial cells is *Escherichia coli*.

10. The method according to claim 1, wherein the nested primer pair comprises SEQ ID No. 21 and SEQ ID No. 10.

11. A method for determining the number of test bacterial cells in a test specimen, comprising:
(1) a first PCR step of carrying out a universal PCR method using a test nucleic acid derived from the test bacterial cells in the test specimen as a template and a universal primer pair for amplifying a bacterial 16S rRNA gene to obtain a universal test amplification product, wherein the universal test amplification product has a sequence comprising an internal sequence, wherein the universal primer pair comprises two forward primers in first equivalent amounts and two reverse primers in second equivalent amounts, wherein the two forward primers differ from each other in a first single base and/or the two reverse primers differ from each other in a second single base;
(2) a second PCR step of carrying out a nested PCR method using a nested primer pair for amplifying the internal sequence to obtain a nested test amplification product;
(3) a bacterial cell number determination step of obtaining a provisional cell number of the test bacterial cells in the test specimen based on the amount of the nested test amplification product and using calibration data indicating a relationship between an amount of at least one nested control amplification product derived from at least one control sample of control bacterial cells of a known species and a cell number of the control bacterial cells in the at least one control sample;
(4) a bacterial species identification step of identifying the species of the test bacterial cells in the test specimen and a 16S rRNA operon copy number in the test bacterial cells; and
(5) a bacterial number correction step of correcting the provisional cell number of the test bacterial cells obtained in step (3) based on the 16S rRNA operon copy number identified in step (4) to determine the number of the test bacterial cells in the test specimen.

12. The method according to claim 11, further comprising the following steps before step (3):
(6) a third PCR step of carrying out a universal PCR method using at least one control nucleic acid derived from the at least one control sample to obtain at least one universal control amplification product;
(7) a fourth PCR step of carrying out a nested PCR method using the at least one universal control amplification product to obtain the at least one nested control amplification product; and
(8) a step of preparing the calibration data based on the cell number of the control bacterial cells in the at least one control sample and the amount of the at least one nested control amplification product.

13. The method according to claim 12, the at least one control sample comprises a plurality of control samples each having a different cell number of the control bacterial cells, the at least one universal control amplification product comprises a plurality of universal control amplification products, and the at least one nested control amplification product comprises a plurality of nested control amplification products,
wherein step (6) comprises
independently using each of a plurality of nucleic acids derived from the plurality of control samples to obtain each of the plurality of universal control amplification products;
wherein step (7) comprises using the plurality of universal control amplification products to obtain the plurality of nested control amplification products;
wherein step (8) comprises preparing a calibration curve based on the cell number of the control bacterial cells in each of the plurality of control samples and the amount of each of the plurality of nested control amplification products; and
wherein step (3) comprises using the calibration curve.

14. The method according to claim 11, wherein step (1) comprises controlling the number of cycles such that gene amplification does not reach a plateau.

15. The method according to claim 11, further comprising diluting a reaction solution to obtain a dilution solution, wherein the reaction solution comprises the universal test amplification product and subjecting the dilution solution to step (2).

16. The method according to claim 12, wherein step (1) and step (6) are carried out concurrently in a first PCR apparatus, and step (2) and step (7) are carried out concurrently in a second PCR apparatus.

17. The method according to claim 11,
wherein step (2) comprises using a plurality of nested primer pairs each independently to obtain a plurality of nested test amplification products, and
wherein step (4) comprises identifying the species of the test bacterial cells in the test specimen based on a combination of melting temperature (Tm) values of the plurality of nested test amplification products or a combination of differences in the Tm values.

18. The method according to claim 12,
wherein step (2) comprises using a plurality of nested primer pairs each independently to obtain a plurality of nested test amplification products,
wherein step (4) comprises identifying the species of the test bacterial cells in the test specimen based on a combination of the melting temperature (Tm) values of the plurality of nested test amplification products or a combination of differences in the Tm values, and wherein step (7) comprises using at least one of the plurality of nested primer pairs or the plurality of nested primer pairs each independently.

19. The method according to claim 11, wherein the known species of the control bacterial cells is *Escherichia coli*.

20. The method according to claim 11, wherein the nested test primer pair comprises SEQ ID No. 21 and SEQ ID No. 10.

21. A method for determining the presence or absence of contamination, comprising:
   (1) a step of centrifuging a test blood specimen to separate a red blood cell fraction, a buffy coat fraction and a plasma fraction, and then preparing sample A consisting of the plasma fraction and the buffy coat fraction, and sample B consisting of the plasma fraction;
   (2) a step of determining the number of test bacterial cells each of sample A and sample B, comprising:
      (a) a first PCR step of carrying out a universal PCR method using a test nucleic acid derived from the test bacterial cells in each of sample A and sample B as a template and a universal primer pair for amplifying a bacterial 16S rRNA gene to obtain a universal test amplification product, wherein the universal test amplification product has a sequence comprising an internal sequence;
      (b) a second PCR step of carrying out a nested PCR method using a nested primer pair for amplifying the internal sequence to obtain a nested test amplification product; and
      (c) a bacterial cell number determination step of obtaining a provisional cell number of the test bacterial cells in each of sample A and sample B based on the amount of the nested test amplification product and using calibration data; and
   (3) a step of determining the presence or absence of contamination of the test bacterial cells in the test blood specimen by comparing the provisional bacterial cell numbers in sample A with that in sample B.

22. The method according to claim 21, wherein step (2) further comprises:
   (d) a bacterial species identification step of identifying the species of the test bacterial cells in the test blood specimen and a 16S rRNA operon copy number in the test bacterial cells; and
   (e) a bacterial cell number correction step of correcting the provisional cell number of the test bacterial cells obtained in step (c) based on the 16S rRNA operon copy number identified in step (d) to determine the cell number of the test bacterial cells in the test blood specimen.

23. The method according to claim 21, wherein step (3) comprises considering an error range of difference between the provisional cell number of the test bacterial cells in sample A and that in sample B.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: Oligonucleotide to act as a primer

<400> SEQUENCE: 1
agagtttgat catggctcag                                              20

<210> SEQ ID NO 2
<211> LENGTH: 20
<212> TYPE: DNA
<213> ORGANISM: Artificial

```
<220> FEATURE:
<223> OTHER INFORMATION: Oligonucleotide to act as a primer

<400> SEQUENCE: 2
agagtttgat cctggctcag                                               20

<210> SEQ ID NO 3
<211> LENGTH: 17
<212> TYPE: DNA
<213> ORGANISM: Artificial
<220> FEATURE:
<223> OTHER INFORMATION: Oligonucleotide to act as a primer

<400> SEQUENCE: 3
ccgggaacgt attcacc                                                  17

<210> SEQ ID NO 4
<211> LENGTH: 18
<212> TYPE: DNA
<213> ORGANISM: Artificial
<220> FEATURE:
<223> OTHER INFORMATION: Oligonucleotide to act as a primer

<400> SEQUENCE: 4
agacccggga acgtattc                                                 18

<210> SEQ ID NO 5
<211> LENGTH: 18
<212> TYPE: DNA
<213> ORGANISM: Artificial
<220> FEATURE:
<223> OTHER INFORMATION: Oligonucleotide to act as a primer

<400> SEQUENCE: 5
aggcccggga acgtattc                                                 18

<210> SEQ ID NO 6
<211> LENGTH: 18
<212> TYPE: DNA
<213> ORGANISM: Artificial
<220> FEATURE:
<223> OTHER INFORMATION: Oligonucleotide to act as a primer

<400> SEQUENCE: 6
cgtaggagtc tggaccgt                                                 18

<210> SEQ ID NO 7
<211> LENGTH: 17
<212> TYPE: DNA
<213> ORGANISM: Artificial
<220> FEATURE:
<223> OTHER INFORMATION: Oligonucleotide to act as a primer

<400> SEQUENCE: 7
gactcctacg ggaggca                                                  17

<210> SEQ ID NO 8
<211> LENGTH: 17
<212> TYPE: DNA
<213> ORGANISM: Artificial
<220> FEATURE:
<223> OTHER INFORMATION: Oligonucleotide to act as a primer

<400> SEQUENCE: 8
tattaccgcg gctgctg                                                  17
```

<210> SEQ ID NO 9
<211> LENGTH: 16
<212> TYPE: DNA
<213> ORGANISM: Artificial
<220> FEATURE:
<223> OTHER INFORMATION: Oligonucleotide to act as a primer

<400> SEQUENCE: 9
agcagccgcg gtaata                                              16

<210> SEQ ID NO 10
<211> LENGTH: 23
<212> TYPE: DNA
<213> ORGANISM: Artificial
<220> FEATURE:
<223> OTHER INFORMATION: Oligonucleotide to act as a primer

<400> SEQUENCE: 10
ggactaccag ggtatctaat cct                                      23

<210> SEQ ID NO 11
<211> LENGTH: 23
<212> TYPE: DNA
<213> ORGANISM: Artificial
<220> FEATURE:
<223> OTHER INFORMATION: Oligonucleotide to act as a primer

<400> SEQUENCE: 11
aacaggatta gatacctgg tag                                       23

<210> SEQ ID NO 12
<211> LENGTH: 21
<212> TYPE: DNA
<213> ORGANISM: Artificial
<220> FEATURE:
<223> OTHER INFORMATION: Oligonucleotide to act as a primer

<400> SEQUENCE: 12
aattaaacca catgctccac c                                        21

<210> SEQ ID NO 13
<211> LENGTH: 21
<212> TYPE: DNA
<213> ORGANISM: Artificial
<220> FEATURE:
<223> OTHER INFORMATION: Oligonucleotide to act as a primer

<400> SEQUENCE: 13
tggtttaatt cgatgcaacg c                                        21

<210> SEQ ID NO 14
<211> LENGTH: 17
<212> TYPE: DNA
<213> ORGANISM: Artificial
<220> FEATURE:
<223> OTHER INFORMATION: Oligonucleotide to act as a primer

<400> SEQUENCE: 14
gagctgacga cagccat                                             17

<210> SEQ ID NO 15
<211> LENGTH: 16
<212> TYPE: DNA
<213> ORGANISM: Artificial
<220> FEATURE:
<223> OTHER INFORMATION: Oligonucleotide to act as a primer

<400> SEQUENCE: 15
ttgggttaag tcccgc                                                        16

<210> SEQ ID NO 16
<211> LENGTH: 16
<212> TYPE: DNA
<213> ORGANISM: Artificial
<220> FEATURE:
<223> OTHER INFORMATION: Oligonucleotide to act as a primer

<400> SEQUENCE: 16
cgtcatcccc accttc                                                        16

<210> SEQ ID NO 17
<211> LENGTH: 20
<212> TYPE: DNA
<213> ORGANISM: Artificial
<220> FEATURE:
<223> OTHER INFORMATION: Oligonucleotide to act as a primer

<400> SEQUENCE: 17
ggctacacac gtgctacaat                                                    20

<210> SEQ ID NO 18
<211> LENGTH: 23
<212> TYPE: DNA
<213> ORGANISM: Artificial
<220> FEATURE:
<223> OTHER INFORMATION: Oligonucleotide to act as a primer

<400> SEQUENCE: 18
gcaggcttaa cacatgcaag tcg                                                23

<210> SEQ ID NO 19
<211> LENGTH: 19
<212> TYPE: DNA
<213> ORGANISM: Artificial
<220> FEATURE:
<223> OTHER INFORMATION: Oligonucleotide to act as a primer

<400> SEQUENCE: 19
gtccagactc ctacgggag                                                     19

<210> SEQ ID NO 20
<211> LENGTH: 17
<212> TYPE: DNA
<213> ORGANISM: Artificial
<220> FEATURE:
<223> OTHER INFORMATION: Oligonucleotide to act as a primer

<400> SEQUENCE: 20
cctacgtatt accgcgg                                                       17

<210> SEQ ID NO 21
<211> LENGTH: 16
<212> TYPE: DNA
<213> ORGANISM: Artificial
<220> FEATURE:
<223> OTHER INFORMATION: Oligonucleotide to act as a primer

<400> SEQUENCE: 21
agcagccgcg gtaata                                                        16

<210> SEQ ID NO 22

```
<211> LENGTH: 18
<212> TYPE: DNA
<213> ORGANISM: Artificial
<220> FEATURE:
<223> OTHER INFORMATION: Oligonucleotide to act as a primer

<400> SEQUENCE: 22
gttaagtccc gcaacgag                                                    18

<210> SEQ ID NO 23
<211> LENGTH: 22
<212> TYPE: DNA
<213> ORGANISM: Artificial
<220> FEATURE:
<223> OTHER INFORMATION: Oligonucleotide to act as a primer

<400> SEQUENCE: 23
ccattgtagc acgtgtgtag cc                                               22

<210> SEQ ID NO 24
<211> LENGTH: 22
<212> TYPE: DNA
<213> ORGANISM: Artificial
<220> FEATURE:
<223> OTHER INFORMATION: Oligonucleotide to act as a primer

<400> SEQUENCE: 24
ggctacacac gtgctacaat gg                                               22
```